United States Patent
Penn et al.

(10) Patent No.: US 11,273,208 B2
(45) Date of Patent: Mar. 15, 2022

(54) CAMKK1 AS A NOVEL REGENERATIVE THERAPEUTIC

(71) Applicants: SUMMA HEALTH, Akron, OH (US); NORTHEAST OHIO MEDICAL UNIVERSITY, Rootstown, OH (US)

(72) Inventors: Marc S. Penn, Beachwood, OH (US); Matthew Kiedrowski, Rootstown, OH (US); Maritza Mayorga, Rootstown, OH (US)

(73) Assignees: Summa Health, Akron, OH (US); Northeast Ohio Medical University, Rootstown, OH (US)

(*) Notice: Subject to any disclaimer, the term of this patent is extended or adjusted under 35 U.S.C. 154(b) by 112 days.

(21) Appl. No.: 15/610,540

(22) Filed: May 31, 2017

(65) Prior Publication Data

US 2017/0340712 A1  Nov. 30, 2017

Related U.S. Application Data

(63) Continuation of application No. PCT/US2015/063118, filed on Dec. 1, 2015.

(60) Provisional application No. 62/086,026, filed on Dec. 1, 2014.

(51) Int. Cl.
| | |
|---|---|
| A61K 38/45 | (2006.01) |
| C12N 9/12 | (2006.01) |
| A61K 38/17 | (2006.01) |
| A61K 35/28 | (2015.01) |
| A61K 45/06 | (2006.01) |
| A61K 48/00 | (2006.01) |

(52) U.S. Cl.
CPC .............. *A61K 38/45* (2013.01); *A61K 35/28* (2013.01); *A61K 38/1709* (2013.01); *A61K 45/06* (2013.01); *C12N 9/12* (2013.01); *C12Y 207/11017* (2013.01); *A61K 48/00* (2013.01)

(58) Field of Classification Search
CPC .... A61K 35/28; A61K 38/1709; A61K 38/45; A61K 45/06; A61K 48/00; C12N 9/12; C12Y 207/11017; A61P 1/16; A61P 11/00; A61P 13/12; A61P 17/02; A61P 19/02; A61P 25/00; A61P 29/00; A61P 3/10; A61P 37/06; A61P 43/00; A61P 9/00; A61P 9/04; A61P 9/10
USPC ........................................................ 435/458
See application file for complete search history.

(56) References Cited

U.S. PATENT DOCUMENTS

| | | | | |
|---|---|---|---|---|
| 6,426,206 B1* | 7/2002 | Wei | ....................... | C12N 9/1205 435/194 |
| 7,764,995 B2* | 7/2010 | Girouard | ............ | A61N 1/36585 607/3 |
| 2002/0168739 A1 | 11/2002 | Wu | | |
| 2008/0213214 A1* | 9/2008 | Terzic | ................. | A61K 38/1825 424/85.2 |
| 2009/0029912 A1 | 1/2009 | Gronthos et al. | | |
| 2009/0246179 A1* | 10/2009 | Penn | ....................... | A61K 35/28 424/93.7 |
| 2011/0020375 A1 | 1/2011 | Five | | |
| 2013/0005037 A1 | 1/2013 | Penn | | |
| 2015/0190429 A1 | 7/2015 | Beelen et al. | | |
| 2017/0340712 A1 | 11/2017 | Penn et al. | | |

FOREIGN PATENT DOCUMENTS

| | | | |
|---|---|---|---|
| EP | 2 687 219 A1 | 1/2014 | |
| WO | WO-2015028900 A1 * | 3/2015 | .............. A61P 19/02 |
| WO | WO-2016/109668 | 7/2016 | |

OTHER PUBLICATIONS

Yano et al., Functional Proteins Involved in Regulation of Intracellular Ca2+ for Drug Development: Role of Calcium/Calmodulin-Dependent Protein Kinases in Ischemic Neuronal Death, Journal Pharmacol. Sci., vol. 97, pp. 351-354. (Year: 2005).*
Ferey et al. Am J Physiol Endocrinol Metab. Oct. 15, 2014; 307(8): E686-E694. Published online Aug. 26, 2014. (Year: 2014).*
Cheng et al. Biochemical Pharmacology 74 (2007) 1758-1765. (Year: 2007).*
Enslen et al. Proc. Nat. Acad. Sci. USA, vol. 93, p. 10803-10808. (Year: 1996).*
Chugh A R et al. (2012), "Administration of cardiac stem cells in patients with ischemic cardiomyopathy: the SCIPIO trial: surgical aspects and interim analysis of myocardial function and viability by magnetic resonance", Circulation, vol. 126, Suppl. 1, pp. S54-S64.
Enslen H et al. (1996), "Regulation of mitogen-activated protein kinsases by a calcium/calmodulin-dependent protein kinase cascade", Proc. Natl. Acad. Sci. USA, vol. 93, pp. 10803-10808.
Fu A et al. (2011), "Neuroprotection in Stroke in the Mouse with Intravenous Erythropoietin-Trojan horse Fusion Protein", vol. 1369, pp. 203-207.
International Search Report and Written Opinion of International Patent Application No. PCT/US2015/063118 dated Mar. 11, 2016, 12 pages.
Matsushita M et al. (1999), "Inhibition of the Ca2+/Calmodulin-dependent Protein Kinase I Cascade by cAMP-dependent Protein Kinase", J. Biol. Chem., vol. 274, No. 15, pp. 10086-10093.
Timmers L et al. (2008), "Reduction of myocardial infarct size by human mesenchymal stem cell conditioned medium", Stem Cell Research 2008, vol. 1, pp. 129-137.
Yano S et al. (2005), "Functional Proteins Involved in Regulation of Intracellular Ca2+ for Drug Development: Role of Calcium/Calmodulin-Dependent Protein Kinases in Ischemic Neuronal Death", J Pharmacol. Sci. 2005, vol. 97, pp. 351-354.
Chen et al., "TGF-β1 attenuates myocardial ischemia-reperfusion injury via inhibition of upregulation of MMP-1", Am J Physiol Heart Circ Physiol, vol. 284, pp. H1612-H1617, May 2003.

(Continued)

*Primary Examiner* — Janet L Epps -Smith
(74) *Attorney, Agent, or Firm* — Foley & Lardner LLP

(57) ABSTRACT

Disclosed herein are methods of treating an ischemic or inflammatory condition in an organ or tissue of a patient comprising inducing an increase of the level of CAMKK1 in said organ or tissue.

14 Claims, 11 Drawing Sheets
Specification includes a Sequence Listing.

(56) References Cited

OTHER PUBLICATIONS

Dong et al., "A Novel Role for CAMKK1 in the Regulation of the Mesenchymal Stem Cell Secretome", Stem Cells Translational Medicine, vol. 6, pp. 1759-1766, 2017.
International Preliminary Report on Patentability dated Jun. 15, 2017 in International Application No. PCT/US2015/063118.
Mayorga et al. "Central Role for Disabled-2 in Mesenchymal Stem Cardiac Protein Expression and Functional Consequences After Engraftment in Acute Myocardial Infarction", Stem Cells and Development, vol. 20, No. 4, pp. 681-693, Apr. 1, 2011.
Mayorga et al., "miR-145 is differentially regulated by TGF-β1 and ischaemia and targets Disabled-2 expression and wnt/β-catenin activity", J. Cell. Mol. Med., vol. 16, No. 5, pp. 1106-1113, 2012.
Nanba et al., "Role of Ca21/Calmodulin-Dependent Protein Kinase—Kinase in Adrenal Aldosterone Production", Endocrinology, vol. 156, No. 5, pp. 1750-1756, May 2015.
Office Action dated Nov. 14, 2011 in U.S. Appl. No. 12/369,491.
Office Action dated May 31, 2017 in Chilean Application No. 201701390 with English Translation.
Office Action dated Jan. 23, 2019 in Israel Application No. 252612 with English Translation.
Bagur R. et al., "Intracellular Ca2 sensing: role in calcium homeostasis and signaling", Mol Cell., 2017, vol. 66, n.6, pp. 780-788.
Extended European Search Report issued in EP Application No. 15864736.2 dated Jul. 16, 2018, 7 pages.
Feng Dong et al., Identification of a Novel Regulator of the Mesenchymal Stem Cell Secretome and Myocardial Repair, Circulation, 2015, vol. 132, N3, Abstract 1879.
Foreign Action other than Search Report on CL 2017001390 dated Oct. 29, 2019.
Foreign Action other than Search Report on EP 15864736.2 dated Jan. 8, 2020.
Foreign Action other than Search Report on RU 2017122817 dated Nov. 29, 2019.
Foreign Action other than Search Reporton RU 2017122817 dated Jun. 11, 2019.
Gnecchi et al., "Evidence supporting paracrine hypothesis for Akt-modified mesenchymal stem cell-mediated cardiac protection and function improvement", The FASEB Journal, Federation of American Societies for Experimental Biology, vol. 20, Jan. 1, 2006, pp. 661-669.
Guest C.B. et al., "Ca2 /calmodulin-dependent kinase kinase alpha is expressed by monocytic cells and regulates the activation profile", PLoS One, 2008, vol. 3(2):el606.
Jun Li et al., "Inhibition of Calcium/Calmodulin Dependent Protein Kinase Kinase is Detrimental in Experimental Stroke", Stroke, 2010, vol. 41, No. 4, e250, 178.
Notice of Rejection issued in JP Application No. 2017-530094 dated Dec. 10, 2019.
Zhao et al: Mesenchymal stem cells with overexpression of midkine enhance cell survival and attenuate cardiac dysfunction in a rat model of myocardial infarction. Stem Cell Research & Therapy. 5(2):37. (Mar. 17, 2014).
Notice of Grounds for Preliminary Rejection issued in KR 10-2017-7018031 dated Mar. 10, 2020, 12 pages.
Berchtold, et al., "The many faces of calmodulin in cell proliferation, programmed cell death, autophagy, and cancer", Biochimica et Biophysica Acta 1843 (2014) 398-435.
Damania et al., "Mesenchymal stromal cell-derived exosome-rich fractionated secretome confers a hepatoprotective effect in liver injury", Stem Cell Research and Therapy, Feb. 6, 2018, vol. 9, No. 31, pp. 1-12.
Furuta, et al., "Mesenchymal Stem Cell-Derived Exosomes Promote Fracture Healing in a Mouse Model," Stem Cells Translational Medicine, vol. 5, No. 12 (Dec. 1, 2016) pp. 1620-1630.
Kang, et al., "Exosomes Secreted from CXCR4 Overexpressing Mesenchymal Stem Cells Promote Cardioprotection via Akt Signaling Pathway following Myocardial Infarction", Stem Cells International, vol. 2015 (May 5, 2015), pp. 1-14.
Ruenn, et al., "Mesenchymal Stem Cell Exosome: A Novel Stem Cell-Based Therapy for Cardiovascular Disease," Regenerative Medicine, vol. 6, No. 4 (Jul. 1, 2011) pp. 481-492.
Tang, et al., "Mesenchymal stem cells over-expressing SDF-1 promote angiogenesis and improve heart function in experimental myocardial infarction in rats," European Journal of Cardio-Thoracic Surgery, vol. 36, No. 4 (Oct. 1, 2009) pp. 644-650.

\* cited by examiner

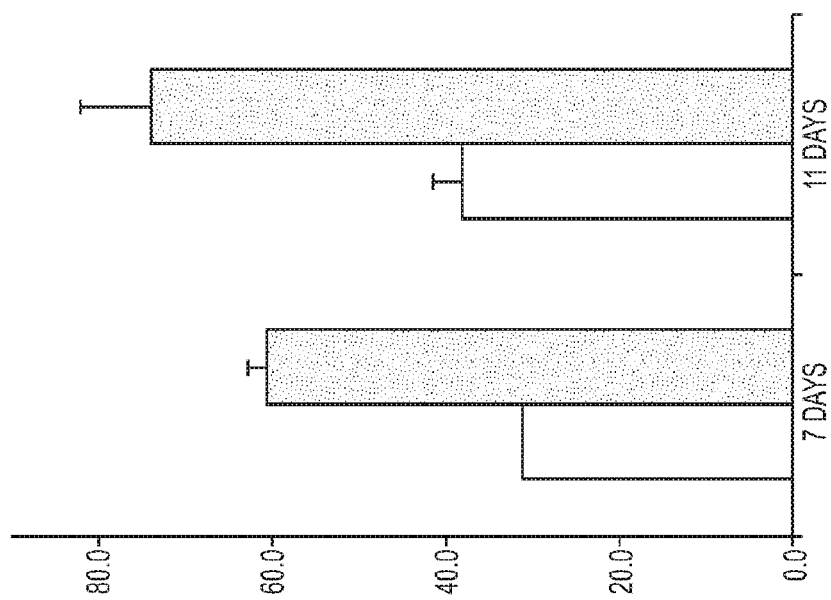

CAMKK1 AS A NOVEL REGENERATIVE THERAPEUTIC

CROSS REFERENCE TO RELATED APPLICATIONS

This application is a continuation application filed under 35 U.S.C. § 111(a) claiming the benefit under 35 U.S.C. §§ 120 and 365(c) of International Application No. PCT/US2015/063118, filed Dec. 1, 2015, which claims the benefit of U.S. Provisional Application No. 62/086,026, filed Dec. 1, 2014, each of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy is named 116449-0211_SL.txt and is 34,111 bytes in size.

TECHNICAL FIELD

The disclosure relates to the use of calcium/calmodulin-dependent protein kinase kinase 1 (CAMKK1) as a novel regenerative therapeutic.

BACKGROUND

Ischemia is a condition wherein the blood flow is completely obstructed or considerably reduced in localized parts of the body, resulting in anoxia, reduced supply of substrates and accumulation of metabolites. Prolonged ischemia results in atrophy, denaturation, apoptosis, and necrosis of affected tissues.

Inflammation is a protective response that is intended to eliminate an initial cause of an injury, as well as necrotic cells/tissues resulting from the injury. In some diseases, such as arthritis, however, inflammation occurs in the absence of an injury. Prolonged inflammation can cause tissue destruction, fibrosis, and/or necrosis.

The goal of regenerative medicine is to induce healing and prevent fibrosis and scar formation following injury through replacement of damaged tissues and induction of endogenous repair pathways.

SUMMARY

Disclosed herein are methods of treating an ischemic or inflammatory condition in an organ or tissue of a patient, comprising inducing an increase of the level of CAMKK1 in said organ or tissue.

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments of the methods; however, the methods are not limited to the specific embodiments disclosed. In the drawings:

FIG. 1A) hCamKK1 full vector. FIG. 1B) hCamKK1 truncated constitutive vector. FIG. 1C) myc hCamKK1 full vector. FIG. 1D) myc hCamKK1 truncated constitutive vector.

FIG. 5A) Cardiac function 14 days after LAD ligation and injection of conditioned media and cells from the indicated treatment. Data represents mean±standard deviation (n=4-8 animals per group). FIG. 5B) The percent±standard deviation left ventricular area expressing collagen as measured by Masson's trichrome stain 14 days after transplantation of MSCs pretreated and transfected with either scramble (control siRNA) or siRNA: CAMKK1. Representative photomicrographs of 4 mm sections are pictured from an animal from each treatment group above each data column. Data are presented as mean±standard deviation. **$P<0.05$ compared with control MSCs. FIG. 5C) Vascular density in the border zone 14 day post-AMI. Confocal image of representative immunofluorescent staining. Endothelial cell staining with isolectin (green), corresponding merged image: Wheat germ agglutinin (red) and DAPI (blue) and Number of vascular density. Data represent mean±SEM (vessels/mm$^2$, n=3 per group). *$P<0.05$ corresponding saline group.

FIG. 6 represents exemplary results from treatment of rats following LAD ligation with a plasmid encoding CAMKK1. Improved cardiac function was observed 1 week and 2 weeks following treatment compared to vehicle (saline or glucose treatment). White bars: saline or glucose treatment; Black bars: CAMKK1 plasmid DNA treatment.

DETAILED DESCRIPTION OF ILLUSTRATIVE EMBODIMENTS

Figure 1B:
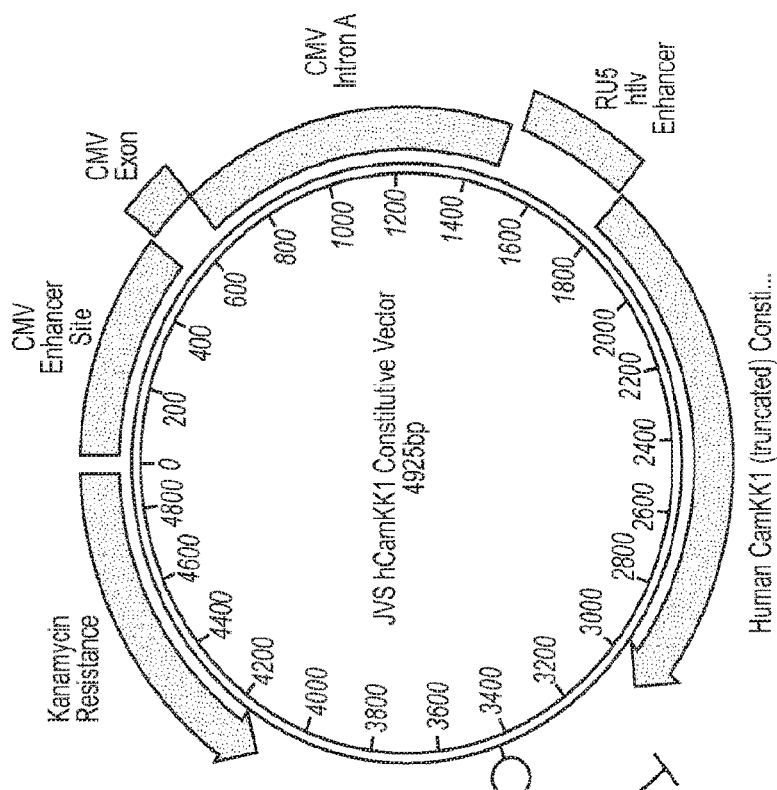
FIG. 1A, FIG. 1B, FIG. 1C, and FIG. 1D illustrate exemplary vector maps for use in the disclosed methods.
Figure 1A:
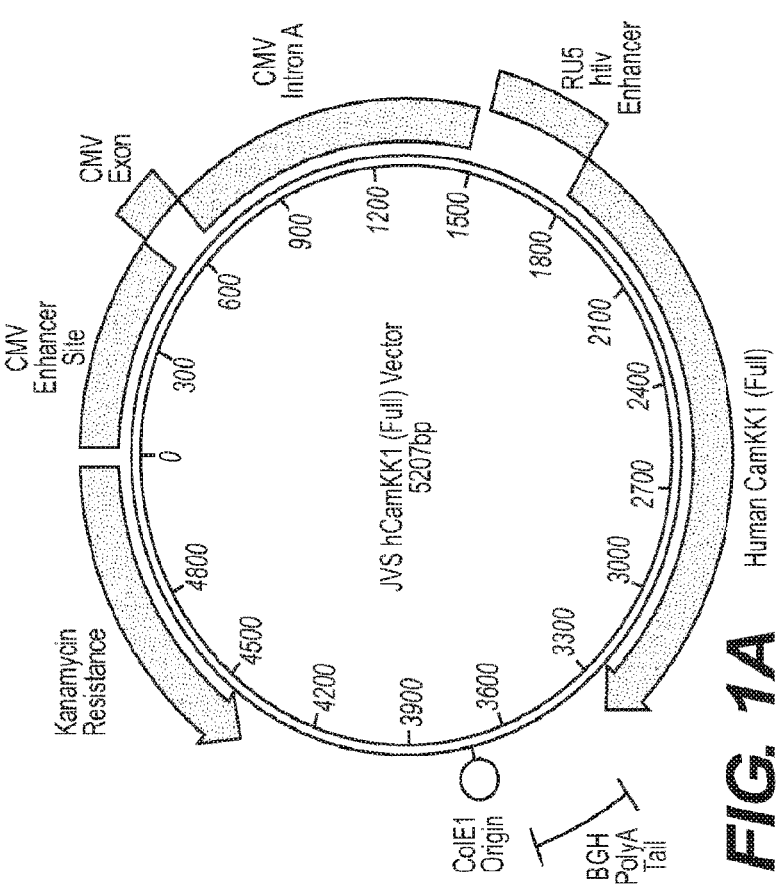
Figures 1C, 1D:
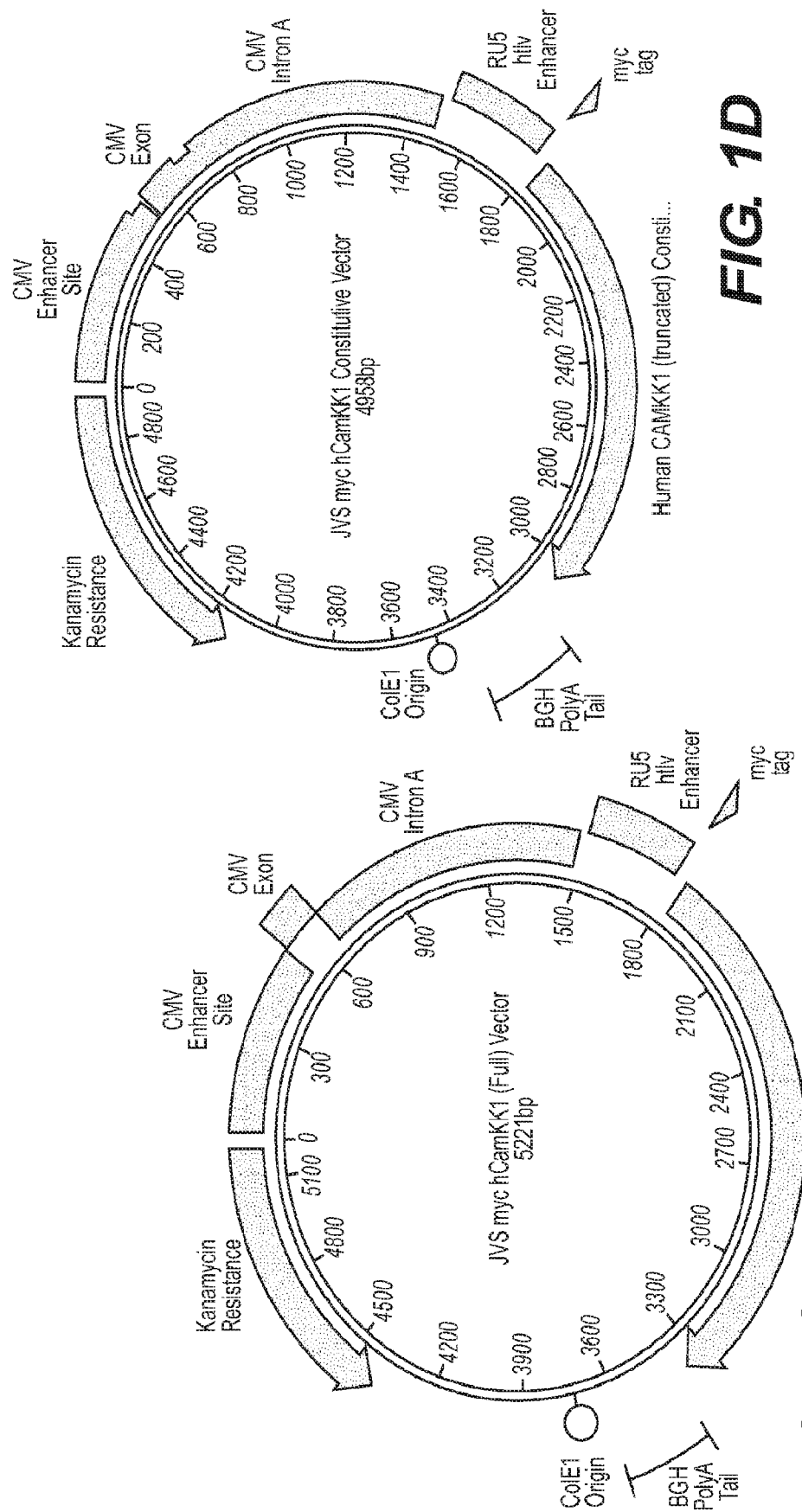

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

Similarly, unless specifically otherwise stated, any description as to a possible mechanism or mode of action or reason for improvement is meant to be illustrative only, and the disclosed methods are not to be constrained by the correctness or incorrectness of any such suggested mechanism or mode of action or reason for improvement.

It is to be appreciated that certain features of the disclosed methods that are, for clarity, described herein in the context of separate embodiments, may also be provided in combination in a single embodiment. Conversely, various features of the disclosed methods that are, for brevity, described in the context of a single embodiment, may also be provided separately or in any subcombination.

As used herein, the singular forms "a," "an," and "the" include the plural.

The following abbreviations are used throughout the disclosure: AMI (acute myocardial infarction); CAMKK1 (calcium/calmodulin-dependent protein kinase kinase 1); Dab2 (disabled homolog 2); MSC (mesenchymal stem cells).

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, "nucleic acid" refers to a polynucleotide containing at least two covalently linked nucleotide or nucleotide analog subunits. A nucleic acid can be a deoxyribonucleic acid (DNA), a ribonucleic acid (RNA), or an analog of DNA or RNA. Nucleotide analogs are commercially available and methods of preparing polynucleotides containing such nucleotide analogs are known (Lin et al. (1994) Nucl. Acids Res. 22:5220-5234; Jellinek et al. (1995) Biochemistry 34: 11363-11372; Pagratis et al. (1997) Nature Biotechnol. 15:68-73). The nucleic acid can be single-stranded, double-stranded, or a mixture thereof. For purposes herein, unless specified otherwise, the nucleic acid is double-stranded, or it is apparent from the context.

As used herein, "treating" and like terms refer to reducing the severity and/or frequency of symptoms from the ischemic or inflammatory condition, eliminating the ischemic or inflammatory condition symptoms and/or the underlying cause of said symptoms, reducing the frequency or likelihood of the ischemic or inflammatory condition symptoms and/or their underlying cause, and improving or remediating damage caused, directly or indirectly, by theischemic or inflammatory condition.

The term "patient" as used herein is intended to mean any animal, in particular, mammals. Thus, the methods are applicable to human and nonhuman animals, although preferably used with mice, rats, and humans, and most preferably with humans.

As used herein, "an increase of the level of CAMKK1" means an amount of CAMKK1 protein in the organ or tissue of the patient that is greater than what is normally present in the organ or tissue of the patient.

Disclosed herein are methods of treating an ischemic or inflammatory condition in an organ or tissue of a patient, comprising inducing an increase of the level of CAMKK1 in said organ or tissue.

CAMKK1 (calcium/calmodulin-dependent protein kinase kinase 1; human CAMKK1 known by UniProtKB number Q8N5S9) belongs to a calcium-triggered signaling cascade and is involved in a number of cellular processes. CAMKK1 is a transferase that belongs to Ser/Thr protein kinase family and CamKK subfamily, and is expressed in heart, pancreas, amygdale, hypothalamus, prostate and lung. CAMKK1 activates CamK1 and CamK4 by phosphorylation of their amino acids Thr(177) and Thr(196), respectively. CAMKK1 activity is itself subjected to regulation by Ca2+/calmodulin; the activity of CAMKK1 is decreased upon phosphorylation by PKA (cAMP-Dependent Protein Kinase) and increased by incubation with PKA in the presence of Ca(2+)/calmodulin but decreased in its absence. This phosphorylation and inhibition of CAMKK1 by PKA is involved in modulating the balance between cAMP- and Ca2+-dependent signal transduction pathways. The nucleic acid sequence and amino acid sequence of CAMKK1 is set forth in SEQ ID NOs:1 and 2, respectively.

Those skilled in the art know that ischemic conditions and inflammatory conditions can occur in a number of different organs in tissues. For example, ischemic conditions can occur in the heart, liver, kidney, brain, spine, lungs, small intestine, large intestine, and arteries. Likewise, inflammatory conditions can occur in the heart, liver, kidney, brain, spine, lungs, intestines, arteries, joints, cartilage, and skin. Accordingly, disclosed are methods of treating an ischemic or inflammatory condition in an organ or tissue of a patient, wherein said organ or tissue is heart, liver, kidney, brain, spine, lungs, small intestine, large intestine, arteries, joints, cartilage, skin, or any combination thereof. In some embodiments, the methods can be used to treat an ischemic or inflammatory condition in the heart. In some embodiments, the methods can be used to treat an ischemic or inflammatory condition in the myocardium. In some embodiments, the methods can be used to treat an ischemic or inflammatory condition in the liver. In some embodiments, the methods can be used to treat an ischemic or inflammatory condition in the kidney. In some embodiments, the methods can be used to treat an ischemic or inflammatory condition in the brain. In some embodiments, the methods can be used to treat an ischemic or inflammatory condition in the spine. In some embodiments, the methods can be used to treat an ischemic or inflammatory condition in the lungs. In some embodiments, the methods can be used to treat an ischemic or inflammatory condition in the small intestine. In some embodiments, the methods can be used to treat an ischemic or inflammatory condition in the large intestine. In some embodiments, the methods can be used to treat an ischemic or inflammatory condition in the arteries. In some embodiments, the methods can be used to treat an ischemic or inflammatory condition in the joints. In some embodiments, the methods can be used to treat an ischemic or inflammatory condition in the cartilage. In some embodiments, the methods can be used to treat an ischemic or inflammatory condition in the skin. In some embodiments, the methods can be used to treat an ischemic or inflammatory condition in any of the above organs or tissues.

Suitable techniques for increasing the level of CAMKK1 in an organ or tissue include, but are not limited to, administering CAMKK1 protein, administering a vector comprising a nucleic acid encoding CAMKK1, administering cells that have been modified to produce an increased level of CAMKK1, administering conditioned media from a culture of cells that have been modified to have an increase of the level of CAMKK1, or any combination thereof.

The increase in the level of CAMKK1 in said organ or tissue can be achieved, for example, by administering CAMKK1 protein to said organ or tissue. Suitable CAMKK1 proteins include wild type CAMKK1 or a constitutively active CAMKK1. In some aspects, the increase in the level of CAMKK1 in said organ or tissue can be achieved by administering wild type CAMKK1 protein to said organ or tissue. For example, the increase in the level of CAMKK1 in said organ or tissue can be achieved by administering wild type CAMKK1 protein to said organ or tissue, wherein the wild type CAMKK1 protein is set for in SEQ ID NO:2. In other aspects, the increase in the level of CAMKK1 in said organ or tissue can be achieved by administering a constitutively active CAMKK1. The constitutively active CAMKK1 can comprise a CAMKK1 1-413 truncation. The increase in the level of CAMKK1 in said organ or tissue can be achieved by administering a CAMKK1 1-413 truncation to said organ or tissue, wherein the CAMKK1 1-413 truncation is set forth in SEQ ID NO:4. Alternatively, the constitutively active CAMKK1 can comprise a T108A mutant, a S459A mutant, or a T108A/S459A mutant CAMKK1. The increase in the level of CAMKK1 in said organ or tissue can be achieved by administering a T108A mutant CAMKK1 to said organ or tissue, wherein the T108A mutant CAMKK1 is set forth in SEQ ID NO:6. The increase in the level of CAMKK1 in said organ or tissue can be achieved by administering a S459A mutant CAMKK1 to said organ or tissue, wherein the S459A mutant CAMKK1 is set forth in SEQ ID NO:8. The increase in the level of CAMKK1 in said organ or tissue can be achieved by administering a T108A/S459A mutant CAMKK1 to said organ or tissue, wherein the T108A/S459A mutant CAMKK1 is set forth in SEQ ID NO:10. Phosphorylation of CAMKK1 by protein kinase A inhibits CAMKK1 activity. Therefore, construction of a constitutively active and non phosphorylatable CAMKK1 by removing one or more of these residues (through, for example, truncation) or mutating Thr108 and Ser459 to alanine, for example, may result in a more potent therapeutic.

The increase in the level of CAMKK1 in said organ or tissue can be achieved by administering a vector comprising a nucleic acid encoding CAMKK1 to said organ or tissue. The vector can comprise a plasmid or a viral vector. In some aspects, the increase in the level of CAMKK1 in the organ or tissue can be achieved by administering a plasmid comprising a nucleic acid encoding CAMKK1. In other aspects, the increase in the level of CAMKK1 in the organ or tissue can be achieved by administering a viral vector comprising a nucleic acid encoding CAMKK1. The nucleic acid can encode wild type CAMKK1 or a constitutively active CAMKK1. In some aspects, the increase in the level of CAMKK1 in the organ or tissue can be achieved by administering a plasmid or viral vector comprising a nucleic acid encoding wild type CAMKK1. For example, the increase in the level of CAMKK1 in the organ or tissue can be achieved by administering a plasmid or viral vector comprising CAMKK1 as set forth in SEQ ID NO:1. In other aspects, the increase in the level of CAMKK1 in the organ or tissue can be achieved by administering a plasmid or viral vector comprising a nucleic acid encoding a constitutively active CAMKK1. The constitutively active CAMKK1 can comprise a CAMKK1 1-413 truncation. For example, the increase in the level of CAMKK1 in the organ or tissue can be achieved by administering a plasmid or viral vector comprising a CAMKK1 1-413 truncation as set forth in SEQ ID NO:3. Alternatively, the constitutively active CAMKK1 can comprise a T108A mutant, a S459A mutant, or a T108A/S459A mutant CAMKK1. For example, the increase in the level of CAMKK1 in the organ or tissue can be achieved by administering a plasmid or viral vector comprising a T108A mutant CAMKK1 as set forth in SEQ ID NO:5. The increase in the level of CAMKK1 in the organ or tissue can be achieved by administering a plasmid or viral vector comprising a S459A mutant CAMKK1 as set forth in SEQ ID NO:7. The increase in the level of CAMKK1 in the organ or tissue can be achieved by administering a plasmid or viral vector comprising a T108A/S459A mutant CAMKK1 as set forth in SEQ ID NO:9.

Suitable vectors for use in the disclosed methods can comprise components or functionalities that further modulate gene delivery and/or gene expression, or that otherwise provide beneficial properties to the targeted cells. Such other components include, for example: components that influence binding or targeting to cells (including components that mediate cell-type or tissue-specific binding); components that influence uptake of the vector by the cell; components that influence localization of the nucleic acid within the cell after uptake (such as agents mediating nuclear localization); and components that influence expression of the nucleic acid. Such components can be provided as a natural feature of the vector (such as the use of certain viral vectors which have components or functionalities mediating binding and uptake), or vectors can be modified to provide such functionalities. Such components also include markers, such as detectable and/or selectable markers that can be used to detect or select for cells that have taken up and are expressing the nucleic acid delivered by the vector. Selectable markers include, for example, ampicillin and kanamycin. In some aspects, the selectable marker can be removed from the vector.

Suitable viral vectors include, but are not limited to, those derived from adenovirus (Ad), adeno-associated virus (AAV), herpes simplex virus (HSV), retrovirus, lentivirus, and alphavirus. Both human and non-human viral vectors can be used. In embodiments wherein human viral vectors are used, the viral vector can be modified to be replication-defective in humans.

The vector comprising a nucleic acid encoding CAMKK1 can be under a constitutively active promoter, a tissue specific promoter, or a drug inducible promoter. For example, a tissue-specific promoter can be fused to the nucleic acid encoding CAMKK1, limiting its expression to a particular tissue.

The nucleic acid encoding CAMKK1 can be introduced into the cells by techniques known in the art including, but not limited to, transfection and electroporation. The vector may be modified to improve transfection or electroporation efficiency.

Exemplary vector maps are illustrated in FIG. 1A-FIG. 1D.

The increase in the level of CAMKK1 in said organ or tissue can be achieved by administering cells that have been modified to produce an increased level of CAMKK1. Cells can be modified to have an increase in the level of CAMKK1 by, for example, modifying the cells with a vector comprising a nucleic acid encoding CAMKK1, modifying the cells with an agent that induces the expression of CAMKK1, or a combination thereof. As discussed above, the CAMKK1 protein can be wild type or a constitutively active CAMKK1. The cells can be modified to express wild type CAMKK1 protein as set forth in SEQ ID NO:2. The cells can be modified to express CAMKK1 1-413 protein as set forth in SEQ ID NO:4. The cells can be modified to express a T108A mutant CAMKK1 as set forth in SEQ ID NO:6. The cells can be modified to express a S459A mutant CAMKK1 as set forth in SEQ ID NO:8. The cells can be modified to express a T108A/S459A mutant CAMKK1 as set forth in SEQ ID NO:10.

In some embodiments, the increase in the level of CAMKK1 in said organ or tissue can be achieved by administering cells that have been modified with a vector comprising a nucleic acid encoding CAMKK1. The vector can comprise a plasmid or a viral vector. In some aspects, the cells can be modified with a plasmid comprising a nucleic acid encoding CAMKK1. In other aspects, the cells can be modified with a viral vector comprising a nucleic acid encoding CAMKK1. As discussed above, the plasmid or viral vector can comprise a nucleic acid encoding wild type or a constitutively active CAMKK1. The cells can be modified with a plasmid or viral vector comprising a nucleic acid encoding wild type CAMKK1 protein, wherein the nucleic acid is set forth in SEQ ID NO:1. The cells can be modified with a plasmid or viral vector comprising a nucleic acid encoding CAMKK1 1-413 protein, wherein the nucleic acid is set forth in SEQ ID NO:3. The cells can be modified with a plasmid or viral vector comprising a nucleic acid encoding a T108A mutant CAMKK1 protein, wherein the nucleic acid is set forth in SEQ ID NO:5. The cells can be modified with a plasmid or viral vector comprising a nucleic acid encoding a S459A mutant CAMKK1 protein, wherein the nucleic acid is set forth in SEQ ID NO:7. The cells can be modified with a plasmid or viral vector comprising a nucleic acid encoding a T108A/S459A mutant CAMKK1 protein, wherein the nucleic acid is set forth in SEQ ID NO:9.

In other embodiments, the increase in the level of CAMKK1 in said organ or tissue can be achieved by administering cells that have been modified with an agent that induces the expression of CAMKK1. Suitable agents for inducing the expression of CAMKK1 include, but are not limited to, TGF-β, miR145, a Dab2 inhibitor, or any combination thereof. In some aspects, the cells can be modified with TGF-β and administered to said organ or tissue. In other aspects, the cells can be modified with miR145 and administered to said organ or tissue. For example, the cells can be modified with a miR145 as set forth in SEQ ID NO:17 and administered to said organ or tissue. In other aspects, the cells can be modified with a Dab2 inhibitor such as, for example, Dab2 siRNA, and administered to said organ or tissue. Suitable Dab2 siRNA include Dab2 siRNA comprising the sense and antisense stands set forth as SEQ ID NO:11 and 12, SEQ ID NO:13 and 14, or SEQ ID NO:15 and 16. For example, the cells can be modified with a Dab2 siRNA as set forth as SEQ ID NO:11 and 12 and administered to said organ or tissue. The cells can be modified with a Dab2 siRNA as set forth as SEQ ID NO:13 and 14 and administered to said organ or tissue. For example, the cells can be modified with a Dab2 siRNA as set forth as SEQ ID NO:15 and 16 and administered to said organ or tissue.

The increase in the level of CAMKK1 in said organ or tissue can be achieved by administering conditioned media from a culture of cells that have been modified to have an increase of the level of CAMKK1. A culture of cells can be modified to have an increase in the level of CAMKK1 by, for example, modifying the cells with a vector comprising a nucleic acid encoding CAMKK1, modifying the cells with an agent that induces the expression of CAMKK1, or a combination thereof. In some embodiments, the increase in the level of CAMKK1 in said organ or tissue can be achieved by administering conditioned media from a culture of cells that have been modified with a vector comprising a nucleic acid encoding CAMKK1. The vector can comprise a plasmid or a viral vector. In some aspects, the culture of cells can be modified with a plasmid comprising a nucleic acid encoding CAMKK1. In other aspects, the culture of cells can be modified with a viral vector comprising a nucleic acid encoding CAMKK1. The methods can comprise administering conditioned media from a culture of cells that have been modified with a plasmid or viral vector comprising a nucleic acid encoding wild type CAMKK1 as set forth in SEQ ID NO:1. The methods can comprise administering conditioned media from a culture of cells that have been modified with a plasmid or viral vector comprising a nucleic acid encoding CAMKK1 1-413 as set forth in SEQ ID NO:3. The methods can comprise administering conditioned media from a culture of cells that have been modified with a plasmid or viral vector comprising a nucleic acid encoding a T108A mutant CAMKK1 as set forth in SEQ ID NO:5. The methods can comprise administering conditioned media from a culture of cells that have been modified with a plasmid or viral vector comprising a nucleic acid encoding a S459A mutant CAMKK1 as set forth in SEQ ID NO:7. The methods can comprise administering conditioned media from a culture of cells that have been modified with a plasmid or viral vector comprising a nucleic acid encoding a T108A/S459A mutant CAMKK1 as set forth in SEQ ID NO:9.

Figure 3:
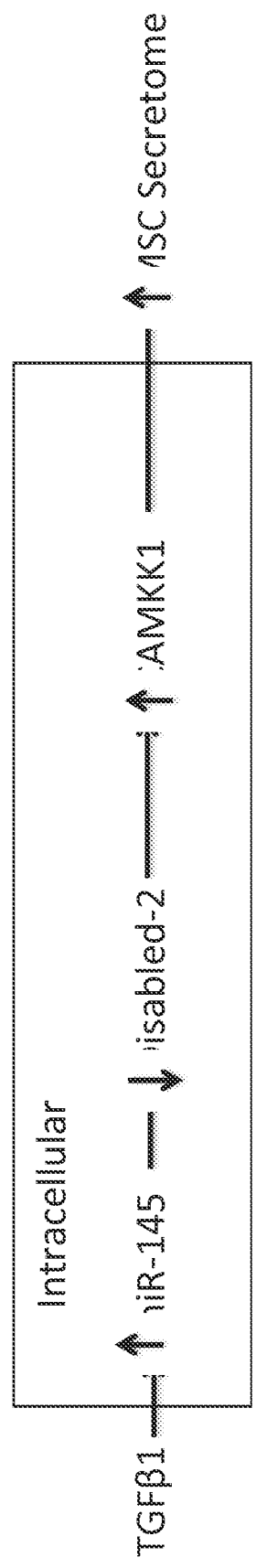
FIG. 3 is an exemplary illustration of the CAMKK1 pathway.

In other embodiments, the increase in the level of CAMKK1 in said organ or tissue can be achieved by administering conditioned media from a culture of cells that have been modified with an agent that induces the expression of CAMKK1. Suitable agents for inducing the expression of CAMKK1 include, but are not limited to, TGF-β, miR145, a Dab2 inhibitor, or any combination thereof. As shown in FIG. 3, TGF-β leads to up regulation of miR-145, miR-145 up regulation leads to down regulation of DAB2, and down regulation of DAB2 leads to up regulation of CAMKK1. In some aspects, the culture of cells can be modified with TGF-β. For example, a the culture of cells can be incubated with TGF-β for a suitable amount of time, the conditioned media or a portion thereof can be harvested, and the conditioned media can be administered to said organ or tissue. In other aspects, the culture of cells can be modified with miR145. For example, the culture of cells can be transfected with miR145, the conditioned media or a portion thereof can be harvested, and the conditioned media can be administered to said organ or tissue. The culture of cells can be transfected with miR145 as set forth in SEQ ID NO:17, the conditioned media or a portion thereof can be harvested, and the conditioned media can be administered to said organ or tissue. In other aspects, the culture of cells can be modified with a Dab2 inhibitor such as, for example, Dab2 siRNA. The culture of cells can be transfected with Dab2 siRNA, the conditioned media or a portion thereof can be harvested, and the conditioned media can be administered to said organ or tissue. The culture of cells can be transfected with Dab2 siRNA as set forth as SEQ ID NO:11 and 12, the conditioned media or a portion thereof can be harvested, and the conditioned media can be administered to said organ or tissue. The culture of cells can be transfected with Dab2 siRNA as set forth as SEQ ID NO:13 and 14, the conditioned media or a portion thereof can be harvested, and the conditioned media can be administered to said organ or tissue. The culture of cells can be transfected with Dab2 siRNA as set forth as SEQ ID NO:15 and 16, the conditioned media or a portion thereof can be harvested, and the conditioned media can be administered to said organ or tissue.

The cells that have been modified to produce an increased level of CAMKK1 or the culture of cells from which the conditioned media is obtained can be mesenchymal stem cells.

The protein, vector, cells, or conditioned media can be administered systemically, directly into the ischemic or inflamed tissue or about the periphery of the ischemic or inflamed tissue. Suitable techniques for systemic administration include enteral administration or parenteral administration (injection, infusion, or implantation). The protein, vector, cells, or conditioned media can be administered, for example, orally, epidurally, intracerebrally, intracerebroventricularly, intraarterially, intraarticularly, intracardially, intramuscularly, intralesionally, intraperitoneally, intrathecally, intravenously, subcutaneously, or any combination thereof.

The ischemic or inflammatory condition can be acute myocardial infarction, heart failure, peripheral artery disease, stroke, liver disease, ischemic kidney disease, multiple sclerosis, traumatic brain injury, spinal cord injury, graft versus host disease (GVHD), diabetes, chronic obstructive pulmonary disease (COPD), rheumatoid arthritis, an injury from a solid organ transplant, an orthopedic injury, a cartilage disorder, a wound, or any combination thereof. Thus, the disclosed methods can be used to treat an ischemic or inflammatory condition in any of the above listed organs or tissues of a patient by inducing an increase of the level of CAMKK1 in said organ or tissue.

The disclosed methods can further comprise administering one or more additional regenerative therapies. Suitable additional regenerative therapies include, but are not limited to, mesenchymal stem cells derived from bone marrow, adipose tissue, placental tissue, umbilical cord, Wharton's Jelly, menstrual blood, stem cells, M2 macrophages, monocytes, or any combination thereof. The stem cells can be neural progenitor cells, endothelial progenitor cells, organ specific endogenous stem cells, or any combination thereof. In some aspects, the methods can further comprise administering neural progenitor cells. In some aspects, the methods can further comprise administering endothelial progenitor cells. In some aspects, the methods can further comprise administering endogenous stem cells, such as cardiac ckit+ cells. In some aspects, the methods can further comprise administering any combination of the above stem cells.

EXAMPLES

The following examples are provided to further describe some of the embodiments disclosed herein. The examples are intended to illustrate, not to limit, the disclosed embodiments.

Figure 2:
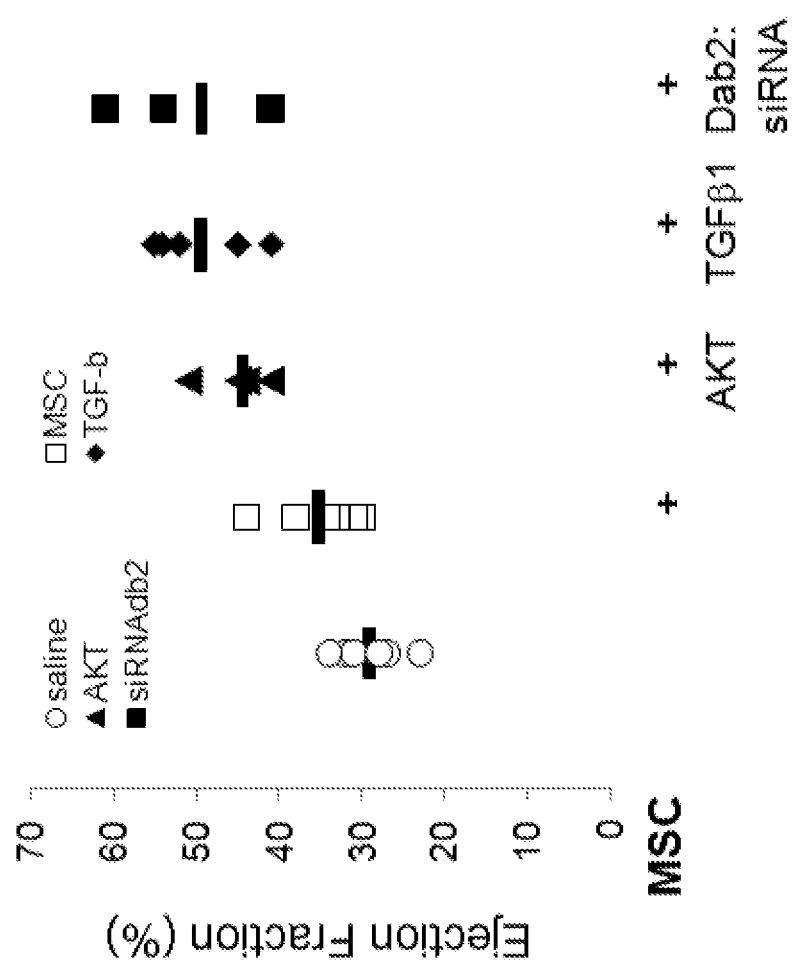
FIG. 2 represents the cardiac function 2 weeks after LAD ligation and injection of conditioned media concentrated from 2 million MSC with the indicated treatment. Data represents individual animals.—represents the mean.

Pretreatment of MSCs with the growth factor transforming growth factor beta (TGF-β) increased the immune suppressive and proangiogenic activity of the cells and resulted in enhanced regenerative capacity (FIG. 2). In a rodent model of AMI, conditioned media collected from TGF-β treated MSCs was delivered to the heart. Improved cardiac function was noted as compared to delivery of conditioned media from untreated MSCs.

Following receptor binding, TGF-β treatment of MSCs cells resulted in a decrease in the expression of disabled homolog 2 (Dab2), a TGF-β1 receptor adaptor protein, that is mediated by an increase in microRNA miR145 (FIG. 3). Decreasing Dab2 expression in MSCs using siRNA also resulted in improved benefit in cardiac function from conditioned media collected from transfected cells (FIG. 2) compared to conditioned media from untreated MSCs when delivered to the heart in a rodent model of AMI. The levels of specific chemokines and growth factors in control and Dab2:siRNA transfected MSC were compared and no differences in FGF-2, PDGF-b, IGF-1, SDF-1 or SFRP-2 were observed (data not shown).

In order to identify the molecular mechanisms which lead to the enhanced secretome of MSCs, an Illumina gene array screen was performed to identify gene changes in response to three different mechanisms of Dab-2 down-regulation: TGF-β treatment, transfection with miR145 and transfection with siRNA against Dab2 compared with untreated cells. In this experiment, cRNA samples from treated cells (TGF-β, mir145, or siRNA Dab2) or untreated cells were hybridized to the Illumina Rat-Ref12 expression BeadChip.

Briefly, the labeled cRNA samples were hybridized to the Illumina RatRef-12 expression BeadChip, which was scanned using Illumina Beadstation GX (Illumina, San Diego, Calif., USA). Each BeadChip contains 22,523 probes that were selected from the National Center for Biotechnology Information (NCBI) Reference Sequence (RefSeq) database. The microarray image was analyzed and intensity data were normalized using Illumina Beadstudio software (Illumina, San Diego, Calif., USA).

To select differentially expressed genes, Welch two sample t-test was performed. The results were combined with fold change and detection p-values to identify differentially expressed genes. Specifically, the selection criterions include the sum of the detection p-values for the three repeats being less than or equal to 0.1, average p-values less than or equal to 0.05, and fold change between control and treated samples greater than or equal to 1.5. In addition, set operations were performed to identify commonly deregulated molecules.

Following the identification of differentially expressing genes, the dataset containing these genes and the corresponding expression values was uploaded into the Ingenuity Systems Pathway Analysis (IPA) software (Ingenuity Systems, Redwood City, Calif.). TGFβ1, miR-145 and Dab2 as well as these differentially expressed genes were marked as focus molecules in IPA. The focus molecules served as seeds and their relationships with other molecules in the Ingenuity Knowledge Base were identified and presented in a set of networks (directed graphs) in which the biological relationship between two molecules (nodes) is represented as a directed edge. In addition, functional and canonical pathway analyses were carried out using IPA. The focus molecules and their closely related genes were analyzed and over-represented functional groups and canonical pathways were identified. Significance of association between these genes and a functional group or a canonical pathway was measured using the p value obtained using Fisher's exact test determining the probability that the association between the focus molecules and the group/pathway is explained by chance alone. A cutoff threshold of 0.05 was used in this study.

Figure 4:
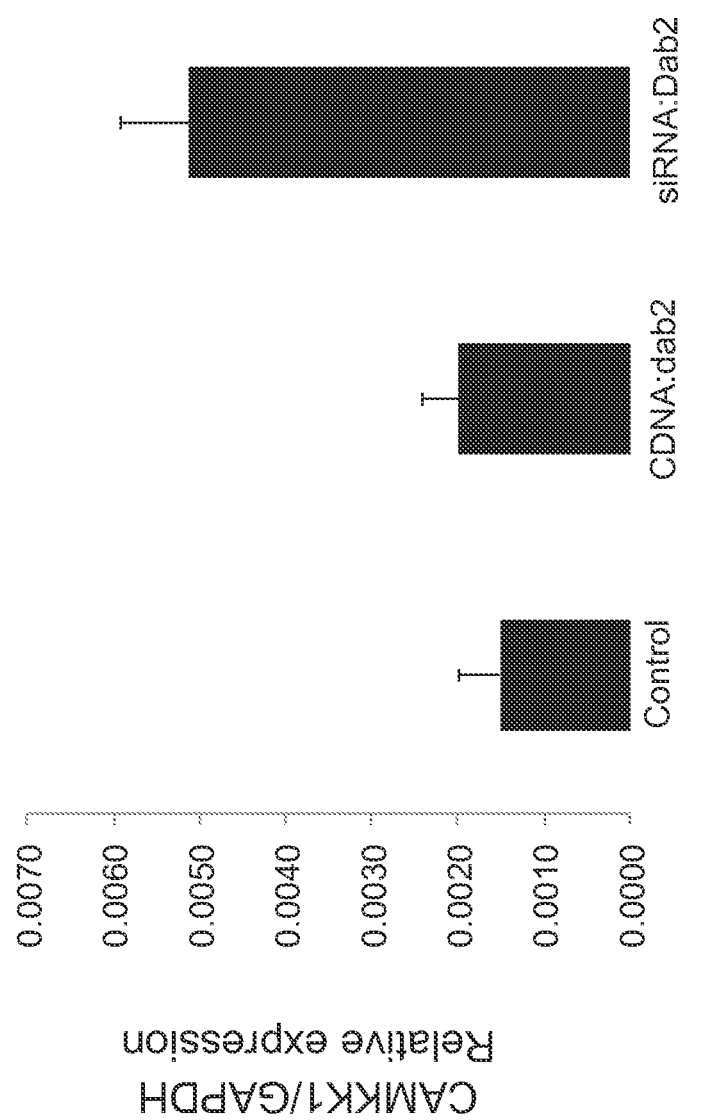
FIG. 4 represents an exemplary analysis of CAMKK1 expression in cells with decreased DAB2 expression (siRNADab2) compared to controls (control or CDNADAb2).

Twenty-three (23) common significant (p<0.05) differentially expressed genes (>1.5 fold difference) were identified from the treated cells compared to the untreated cells (Table 1). Pathway analysis identified one gene, calcium/calmodulin-dependent protein kinase kinase 1 (CAMKK1), downstream of miR145, TGF-β signaling and dab-2 downregulation, that is shown herein to modulate the MSC secretome and function. An independent experiment confirmed that downregulation of Dab2 results in upregulation of CAMKK1 expression and associated with an upregulation in CAMKK1 protein (FIG. 4).

TABLE 1

Analysis of Differentially Expressed Genes under Treatment with siRNA: Dab2, miRNA145, or TGFβ

| Entrez Gene Name (Symbol) | Avg Fold Change | Avg p_value | Location |
|---|---|---|---|
| annexin A3 (ANXA3) | −22.07 | 0.03 | Cytoplasm |
| Rho GDP dissociation inhibitor (GDI) beta (ARHGDIB) | −19.47 | 0.01 | Cytoplasm |
| BCL2-related protein A1 (BCL2A1) | −4.31 | 0.00 | Cytoplasm |
| ATPase, H+ transporting, lysosomal 42 kDa, V1 subunit C1 (ATP6V1C1) | −3.83 | 0.02 | Cytoplasm |
| ATP-binding cassette, sub-family B (MDR/TAP), member 9 (ABCB9) | −2.95 | 0.02 | Cytoplasm |
| carbonic anhydrase III, muscle specific (CA3) | −2.54 | 0.01 | Cytoplasm |
| calcium/calmodulin-dependent protein kinase kinase 1, alpha (CAMKK1) | 1.72 | 0.01 | Cytoplasm |
| apolipoprotein E (APOE) | −23.52 | 0.01 | Extracellular |
| complement component 1, q sub-component, C chain (C1QC) | −14.50 | 0.03 | Extracellular |
| complement component 1, q sub-component, A chain (C1QA) | −5.65 | 0.01 | Extracellular |
| ADAM metallopeptidase with thrombospondin type 1 motif, 1 (ADAMTS1) | 2.51 | 0.01 | Extracellular |
| allograft inflammatory factor 1 (AIF1) | −15.20 | 0.02 | Nucleus |
| carbonic anhydrase IX (CA9) | −10.81 | 0.02 | Nucleus |
| CD68 molecule (CD68) | −20.28 | 0.01 | Membrane |
| CD83 molecule (CD83) | −6.66 | 0.02 | Membrane |
| arachidonate 5-lipoxygenase-activating protein (ALOX5AP) | −3.36 | 0.02 | Membrane |
| arginine vasopressin receptor 1A (AVPR1A) | −2.98 | 0.02 | Membrane |
| amyloid beta (A4) precursor protein (App) | −2.39 | 0.02 | Membrane |
| alanine and arginine rich domain containing protein (AARD) | −27.08 | 0.02 | unknown |
| ADP-ribosylation factor-like 11 (ARL11) | −6.77 | 0.01 | unknown |
| Cd300 molecule-like family member E, pseudogene 1 (Cd3001e-ps1) | −4.08 | 0.01 | unknown |
| armadillo repeat containing, X-linked 2 (ARMCX2) | −2.78 | 0.01 | unknown |
| arginine vasopressin-induced 1 (AVPI1) | −1.78 | 0.01 | unknown |

Real-time PCR was performed to confirm that the down-regulation of Dab2 leads to up-regulation of CAMKK1 from MSC in culture (data not shown). Western blot analysis confirmed that this up-regulation was associated with an increase in CAMKK1 protein expression (data not shown).

Figure 5A:
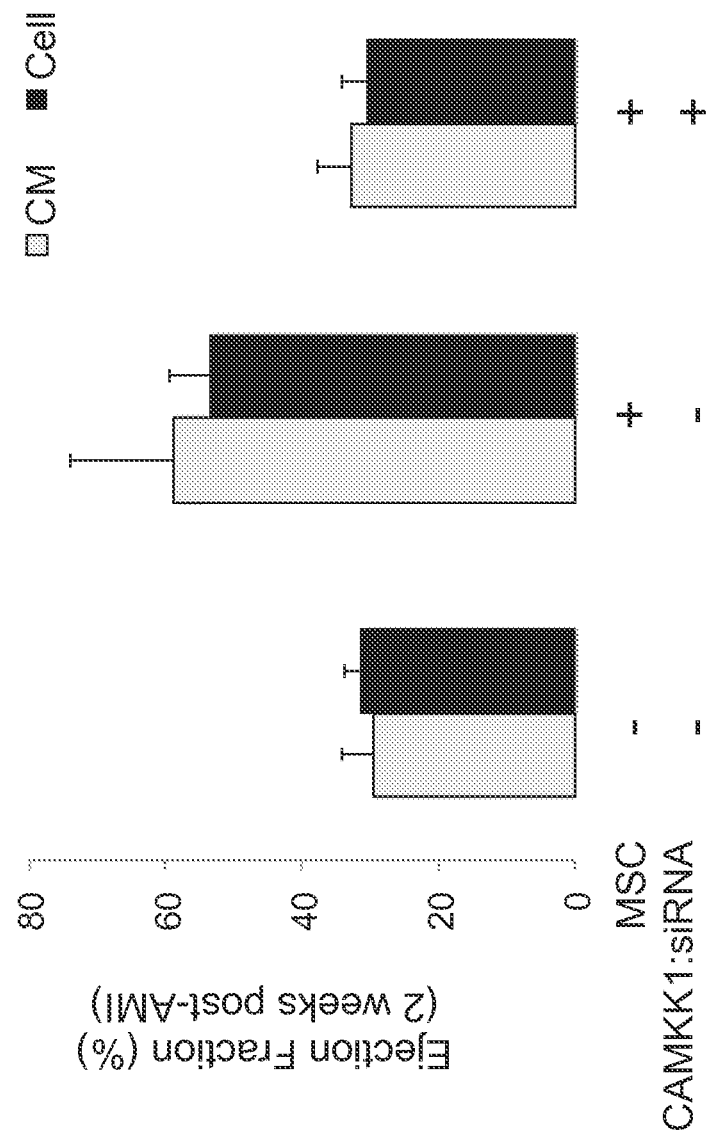
FIG. 5A-FIG. 5C represent.

CAMKK1 has not previously been demonstrated to be involved in inducing or enhancing endogenous regenerative pathways. To demonstrate the role of CAMKK1 in modulating the MCS secretome, CAMKK1 expression was down-regulated in MSCs through transfection with CAMKK1 siRNA. The data in FIG. 5A show that the injection of 2 million MSC or the concentrated condition media from 2 million MSC into the infarct border zone at the time of LAD ligation results in inhibition of MSC mediated preservation of left ventricular function, specifically, a 30% and 20% increase in cardiac function, respectively, 14 days after AMI. In the absence of CAMKK1, however, there is no significant increase in cardiac function in response to the injection of MSC or MSC conditioned media (FIG. 5A). To begin to understand how the absence of CAMKK1 altered myocardial response to MSC injection, the area of collagen deposition and vascular density in response to MSC and MSC conditioned media injections was quantified. An increase in collagen deposition (FIG. 5B) and a blunting in the increase in vascular density (FIG. 5C) was observed in response to MSC transfected with CAMKK1:siRNA compared to control MSC. These data demonstrate that modulation of CAMKK1 does alter the MSC secretome and subsequent myocardial repair through potentially multiple mechanisms. Importantly, the down-regulation of CAMKK1 in TGF-β1 pretreated MSC also rendered the conditioned from these cells inactive (data not shown).

To begin to define paracrine factors that are modulated by CAMKK1 expression in MSC, conditioned media from MSC transfected with scramble or CAMKK1:siRNA was assayed. The media was conditioned for 24 hours, beginning 24 hours after transfection. The media was concentrated as though for intracardiac injection. The concentrated conditioned media was assayed using a nylon based cytokine array. Consistent with the hypothesis that up-regulation of CAMKK1 is pro-healing, down-regulation of CAMKK1 resulted in the up-regulation of 5 cytokines, 4 of which are related to inflammatory cell recruitment.

To test whether activation of the CAMKK1 pathway can result in enhanced regenerative capacity of other cells types, a plasmid encoding CAMKK1 downstream of the CMV promoter was developed and utilized to demonstrate that upregulation of CAMKK1 activity can result in improved cardiac function. Following induction of an AMI in rodents by LAD ligation, CAMKK1 encoding plasmid (KCP-CAMKK1) or vehicle was injected directly into the heart into the peri-infarct area. Cardiac function was measured 1 week and 2 weeks later and resulted in improvement in cardiac function as measured by echocardiography in KCP-CAMKK1 treated animals compared to vehicle (saline or glucose) treated animals (FIG. 6). Taken together, the data demonstrate that activation of CAMKK1 signaling pathway through overexpression of CAMKK1 results in enhanced regeneration in the heart.

Figure 8A:
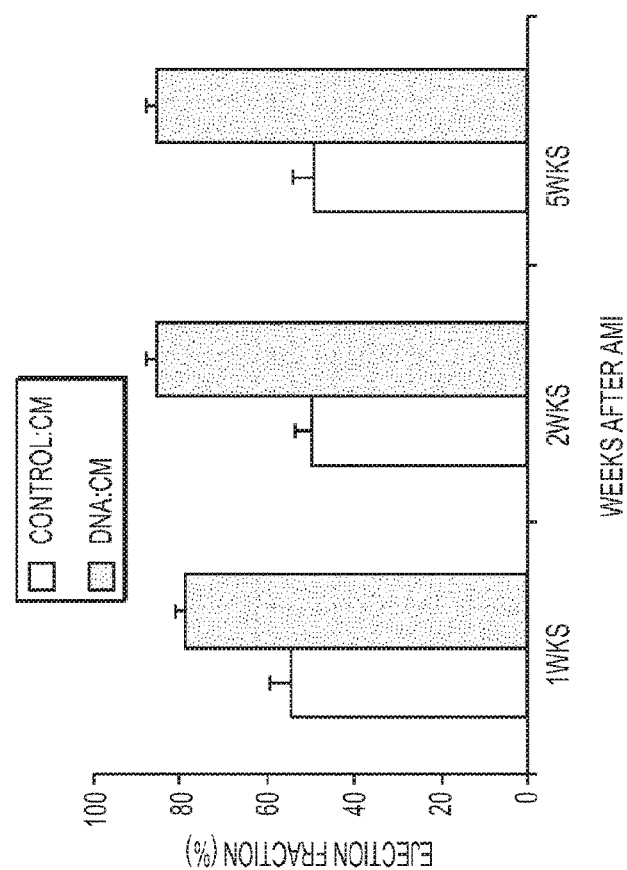
FIG. 8A and FIG. 8B illustrate the effects of CAMKK1 (DNA) over-expression in MSC on MSC and MSC conditioned media on Ejection Fraction in rodent model of AMI. Control was MSC transfected with marker cDNA. Echocardiography was performed at 1, 2 and 5 weeks after AMI. Y-axis is EF (%), mean±SD.
Figure 8B:
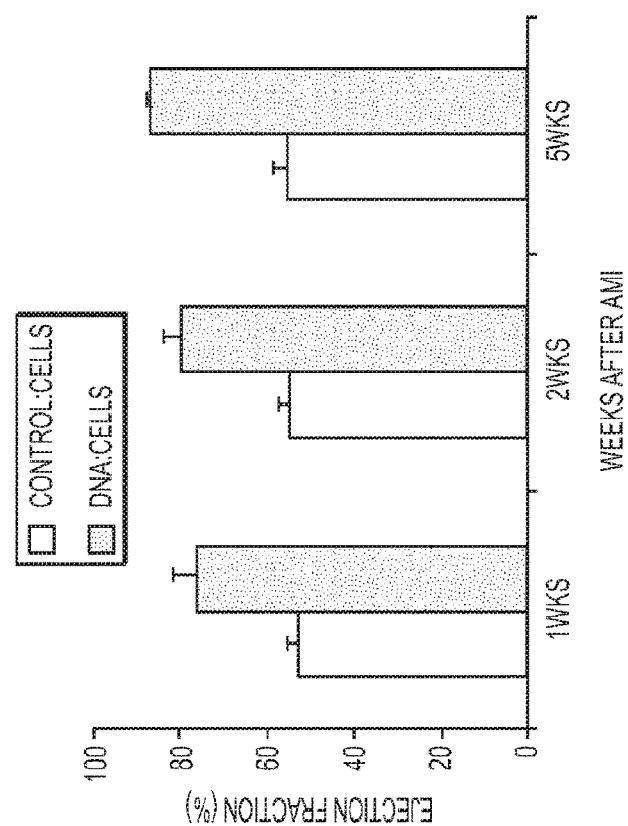

To determine if the up-regulation of CAMKK1 was sufficient to induce tissue repair, studies with control and CAMKK1 over-expressing MSC and conditioned media from control and CAMKK1 over-expressing MSC were performed. The data in FIG. 8A and FIG. 8B demonstrate that the over-expression of CAMKK1 in MSC enhanced MSC and MSC conditioned media function in AMI.

Figure 7:
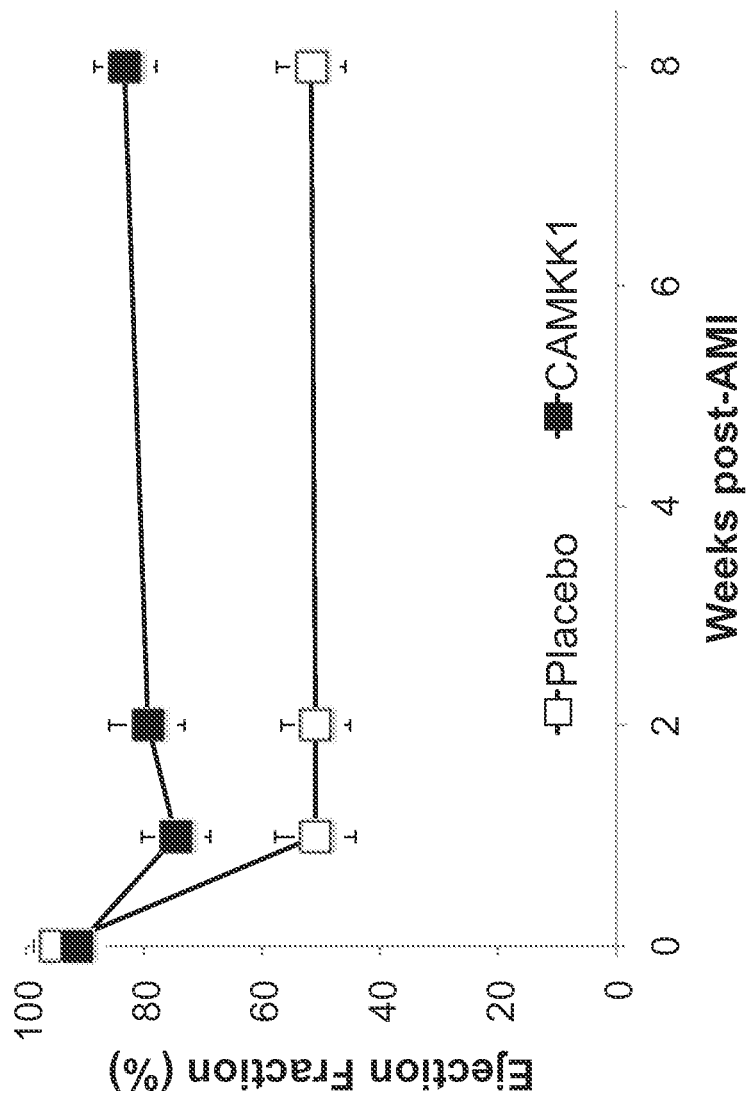
FIG. 7 illustrates the effects of CAMKK1 (DNA) overexpression on Ejection Fraction in rodent model of AMI. 30 animals were submitted to anterior wall myocardial infarction via direct LAD ligation. Following ligation of the LAD, the animals were randomized and injected with 0.5 mg of CAMKK1 plasmid or saline in 5 divided 50-100 μl injections. One week, two weeks, and 8 weeks post-LAD ligation the animals underwent echocardiography and ejection fraction was calculated based on a parasternal long-axis view of the heart. All investigators performing LAD ligation, drug injection and echocardiography were blinded to treatment group of any animal. (n=12 for placebo; n=15 for CAMKK1). Placebo was injected with saline. Mean±SD.

Whether CAMKK1 over-expression in the absence of MSC could lead to MSC like effects on the left ventricle in the setting of AMI was evaluated by generating a cDNA expression vector that used the CMV promoter to overexpress CAMKK1. 5×100 ug injections of plasmid cDNA were delivered around the infarct border zone at the time of LAD ligation. LV function as a function of time after AMI was quantified. As shown in FIG. 7 CAMKK1 over-expression in the absence of MSC led to significant preservation or recovery of LV function.

Figure 5B:
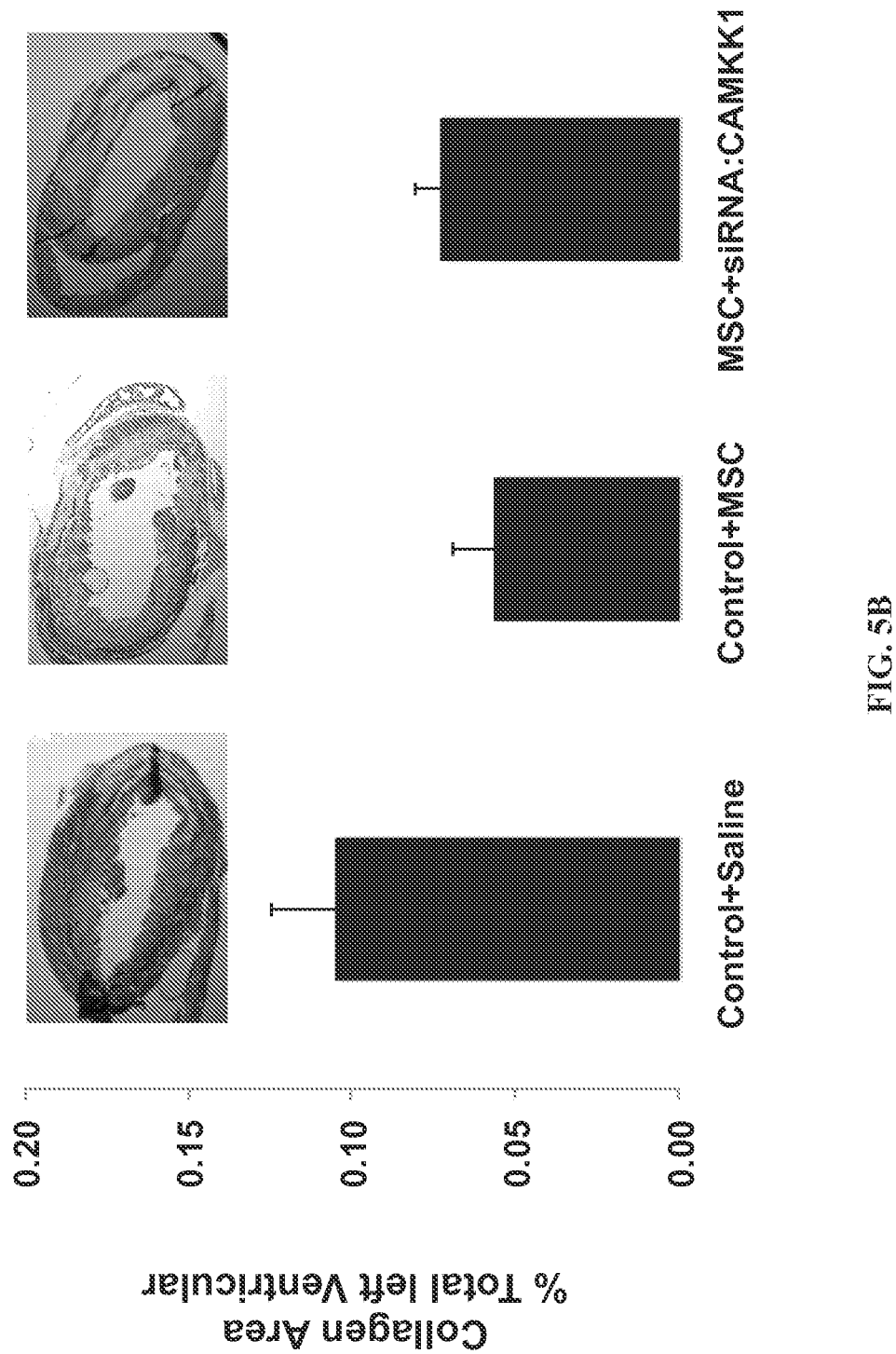
Figure 5C:
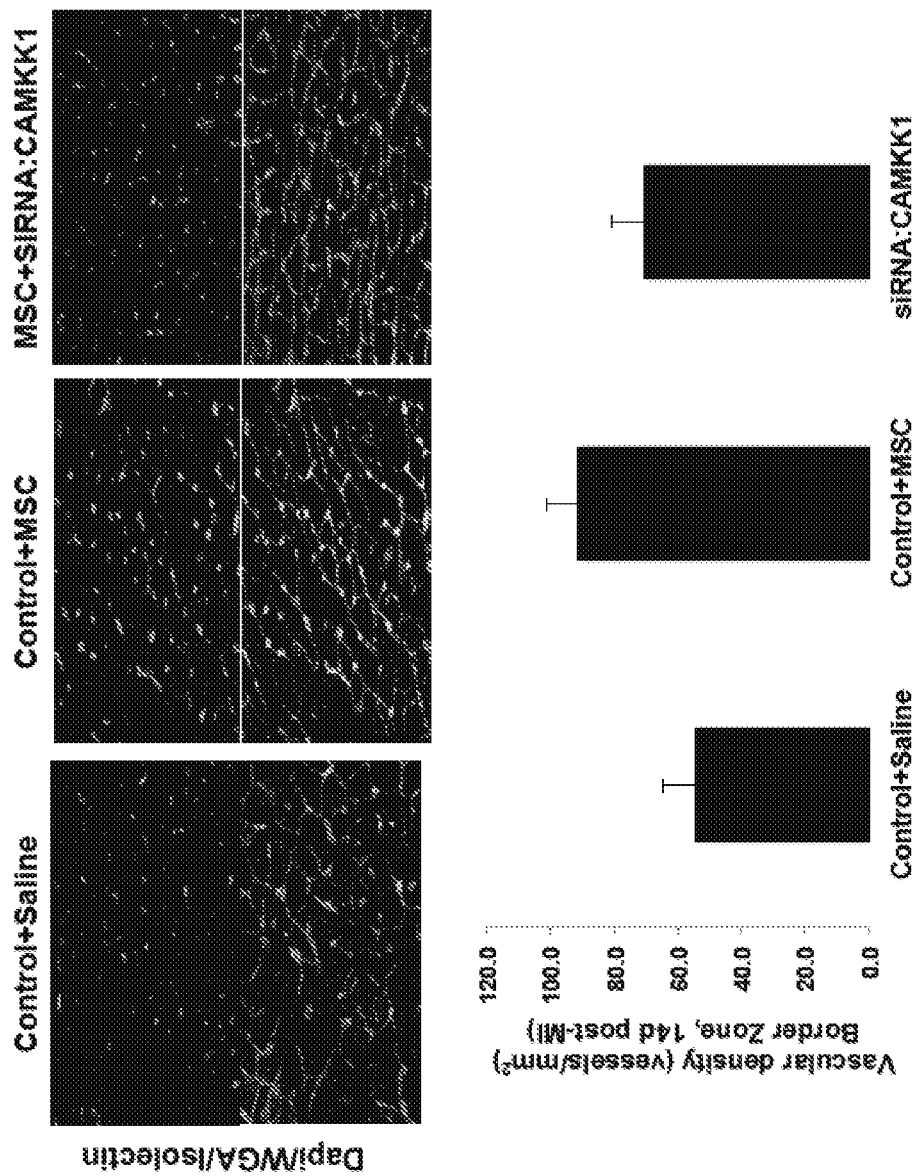

Histological analyses (data not shown) of the tissue at the end of the experiments displayed in FIGS. 5B and C demonstrated that CAMKK1 consistently led to:
 a decrease in infarct size and myocardial fibrosis as measured by Mason's trichrome stain;
 an increase in vascular density in the infarct border zone.

There is no effect of CAMKK1 on SDF-1, or SDF-1 on CAMKK1 expression (data not shown). The CAMKK1 approach appears to have the potential to be completely synergistic and not redundant to SDF-1.

Summary

As disclosed herein, CAMKK1 was identified as a key regulator of MSC function. The fact that the SDF-1:CXCR4 axis and CAMKK1 have no molecular overlap with respect to induced expression suggests that a combination of CAMKK1 and SDF-1 should have synergistic effects, most obviously in acute injury, and likely in chronic tissue injury.

The disclosed methods induce the enhancement of the regenerative secretome (secreted molecules) from multiple cell types, including MSCs. Without intending to be bound by theory, it is believed that the increased levels of CAMKK1 result in enhanced functional benefit through alteration of secreted factors from those cells expressing CAMKK1. This secretome induction can be used as a novel regenerative therapeutic.

Those skilled in the art will appreciate that numerous changes and modifications can be made to the preferred embodiments and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

TABLE 2

| | Sequences |
|---|---|
| CAMKK1 nucleic acid (NM_032294) | ATGGAGGGGGGTCCAGCTGTCTGCTGCCAGGATCCTCGGGCAGAGCTGGTAGAACGGGTGGCAGCCA<br>TCGATGTGACTCACTTGGAGGAGGCAGATGGTGGCCCAGAGCCTACTAGAAACGGTGTGGACCCCCC<br>ACCACGGGCCAGAGCTGCCTCTGTGATCCCTGGCAGTACTTCAAGACTGCTCCCAGCCCGGCCTAGCC<br>TCTCAGCCAGGAAGCTTTCCCTACAGGAGCGGCCAGCAGGAAGCTATCTGGAGGCGCAGGCTGGGCC<br>TTATGCCACGGGGCCTGCCAGCCACATCTCCCCCCGGGCCTGGCGGAGGCCCACCATCGAGTCCCACC<br>ACGTGGCCATCTCAGATGCAGAGGACTGCGTGCAGCTGAACCAGTACAAGCTGCAGAGTGAGATTGG<br>CAAGGGTGCCTACGGTGTGGTGAGGCTGGCCTACAACGAAAGTGAAGACAGACACTATGCAATGAAA<br>GTCCTTTCCAAAAAGAAGTTACTGAAGCAGTATGGCTTTCCACGTCGCCCTCCCCCGAGAGGGTCCCA<br>GGCTGCCCAGGGAGGACCAGCCAAGCAGCTGCTGCCCCTGGAGCGGGTGTACCAGGAGATTGCCATC<br>CTGAAGAAGCTGGACCACGTGAATGTGGTCAAACTGATCGAGGTCCTGGATGACCCAGCTGAGGACA<br>ACCTCTATTTGGTGTTTGACCTCCTGAGAAAGGGGCCCGTCATGGAAGTGCCCTGTGACAAGCCCTTC<br>TCGGAGGAGCAAGCTCGCCTCTACCTGCGGGACGTCATCCTGGGCCTCGAGTACTTGCACTGCCAGAA<br>GATCGTCCACAGGGACATCAAGCCATCCAACCTGCTCCTGGGGGATGATGGGCACGTGAAGATCGCC<br>GACTTTGGCGTCAGCAACCAGTTTGAGGGGAACGACGCTCAGCTGTCCAGCACGGCGGGAACCCCAG<br>CATTCATGGCCCCCGAGGCCATTTCTGATTCCGGCCAGAGCTTCAGTGGGAAGGCCTTGGATGTATGG<br>GCCACTGGCGTCACGTTGTACTGCTTTGTCTATGGGAAGTGCCCATTCATCGACGATTTCATCCTGGCC<br>CTCCACAGGAAGATCAAGAATGAGCCCGTGGTGTTTCCTGAGGAGCCAGAAATCAGCGAGGAGCTCA<br>AGGACCTGATCCTGAAGATGTTAGACAAGAATCCCGAGACGAGAATTGGGGTGCCAGACATCAAGTT<br>GCACCCTTGGGTGACCAAGAACGGGGAGGAGCCCCTTCCTTCGGAGGAGGAGCACTGCAGCGTGGTG<br>GAGGTGACAGAGGAGGAGGTTAAGAACTCAGTCAGGCTCATCCCCAGCTGGACCACGGTGATCCTGG<br>TGAAGTCCATGCTGAGGAAGCGTTCCTTTGGGAACCCGTTTGAGCCCCAAGCACGGAGGGAAGAGCG<br>ATCCATGTCTGCTCCAGGAAACCTACTGGTGAAAGAAGGGTTTGGTGAAGGGGGCAAGAGCCCAGAG<br>CTCCCCGGCGTCCAGGAAGACGAGGCTGCATCCTGA<br>(SEQ ID NO: 1) |
| CAMKK1 protein | MEGGPAVCCQDPRAELVERVAAIDVTHLEEADGGPEPTRNGVDPPPRARAASVIPGSTSRLLPARPSLSAR<br>KLSLQERPAGSYLEAQAGPYATGPASHISPRAWRRPTIESHHVAISDAEDCVQLNQYKLQSEIGKGAYGVV<br>RLAYNESEDRHYAMKVLSKKKLLKQYGFPRRPPPRGSQAAQGGPAKQLLPLERVYQEIAILKKLDHVNVV<br>KLIEVLDDPAEDNLYLVFDLLRKGPVMEVPCDKPFSEEQARLYLRDVILGLEYLHCQKIVHRDIKPSNLLLG<br>DDGHVKIADFGVSNQFEGNDAQLSSTAGTPAFMAPEAISDSGQSFSGKALDVWATGVTLYCFVYGKCPFI<br>DDFILALHRKIKNEPVVFPEEPEISEELKDLILKMLDKNPETRIGVPDIKLHPWVTKNGEEPLPSEEEHCSVV<br>EVTEEEVKNSVRLIPSWTTVILVKSMLRKRSFGNPFEPQARREERSMSAPGNLLVKEGFGEGGKSPELPGV<br>QEDEAAS<br>(SEQ ID NO: 2) |
| CAMKK1 1-413 nucleic acid | ATGGAGGGGGGTCCAGCTGTCTGCTGCCAGGATCCTCGGGCAGAGCTGGTAGAACGGGTGGCAGCCA<br>TCGATGTGACTCACTTGGAGGAGGCAGATGGTGGCCCAGAGCCTACTAGAAACGGTGTGGACCCCCC<br>ACCACGGGCCAGAGCTGCCTCTGTGATCCCTGGCAGTACTTCAAGACTGCTCCCAGCCCGGCCTAGCC<br>TCTCAGCCAGGAAGCTTTCCCTACAGGAGCGGCCAGCAGGAAGCTATCTGGAGGCGCAGGCTGGGCC<br>TTATGCCACGGGGCCTGCCAGCCACATCTCCCCCCGGGCCTGGCGGAGGCCCACCATCGAGTCCCACC<br>ACGTGGCCATCTCAGATGCAGAGGACTGCGTGCAGCTGAACCAGTACAAGCTGCAGAGTGAGATTGG<br>CAAGGGTGCCTACGGTGTGGTGAGGCTGGCCTACAACGAAAGTGAAGACAGACACTATGCAATGAAA<br>GTCCTTTCCAAAAAGAAGTTACTGAAGCAGTATGGCTTTCCACGTCGCCCTCCCCCGAGAGGGTCCCA<br>GGCTGCCCAGGGAGGACCAGCCAAGCAGCTGCTGCCCCTGGAGCGGGTGTACCAGGAGATTGCCATC<br>CTGAAGAAGCTGGACCACGTGAATGTGGTCAAACTGATCGAGGTCCTGGATGACCCAGCTGAGGACA<br>ACCTCTATTTGGTGTTTGACCTCCTGAGAAAGGGGCCCGTCATGGAAGTGCCCTGTGACAAGCCCTTC<br>TCGGAGGAGCAAGCTCGCCTCTACCTGCGGGACGTCATCCTGGGCCTCGAGTACTTGCACTGCCAGAA<br>GATCGTCCACAGGGACATCAAGCCATCCAACCTGCTCCTGGGGGATGATGGGCACGTGAAGATCGCC<br>GACTTTGGCGTCAGCAACCAGTTTGAGGGGAACGACGCTCAGCTGTCCAGCACGGCGGGAACCCCAG<br>CATTCATGGCCCCCGAGGCCATTTCTGATTCCGGCCAGAGCTTCAGTGGGAAGGCCTTGGATGTATGG<br>GCCACTGGCGTCACGTTGTACTGCTTTGTCTATGGGAAGTGCCCATTCATCGACGATTTCATCCTGGCC<br>CTCCACAGGAAGATCAAGAATGAGCCCGTGGTGTTTCCTGAGGAGCCAGAAATCAGCGAGGAGCTCA<br>AGGACCTGATCCTGAAGATGTTAGACAAGAATCCCGAGACGAGAATTGGGGTGCCAGACATCAAGTT<br>GCACCCTTGGGTGACCAAGAACGGGTGA<br>(SEQ ID NO: 3) |
| CAMKK1 1-413 protein | MEGGPAVCCQDPRAELVERVAAIDVTHLEEADGGPEPTRNGVDPPPRARAASVIPGSTSRLLPARPSLSAR<br>KLSLQERPAGSYLEAQAGPYATGPASHISPRAWRRPTIESHHVAISDAEDCVQLNQYKLQSEIGKGAYGVV<br>RLAYNESEDRHYAMKVLSKKKLLKQYGFPRRPPPRGSQAAQGGPAKQLLPLERVYQEIAILKKLDHVNVV<br>KLIEVLDDPAEDNLYLVFDLLRKGPVMEVPCDKPFSEEQARLYLRDVILGLEYLHCQKIVHRDIKPSNLLLG<br>DDGHVKIADFGVSNQFEGNDAQLSSTAGTPAFMAPEAISDSGQSFSGKALDVWATGVTLYCFVYGKCPFI<br>DDFILALHRKIKNEPVVFPEEPEISEELKDLILKMLDKNPETRIGVPDIKLHPWVTKNG<br>(SEQ ID NO: 4) |

TABLE 2-continued

Sequences

CAMKK1 T108A
nucleic acid
ATGGAGGGGGGTCCAGCTGTCTGCTGCCAGGATCCTCGGGCAGAGCTGGTAGAACGGGTGGCAGCCA
TCGATGTGACTCACTTGGAGGAGGCAGATGGTGGCCCAGAGCCTACTAGAAACGGTGTGGACCCCCC
ACCACGGGCCAGAGCTGCCTCTGTGATCCCTGGCAGTACTTCAAGACTGCTCCCAGCCCGGCCTAGCC
TCTCAGCCAGGAAGCTTTCCCTACAGGAGCGGCCAGCAGGAAGCTATCTGGAGGCGCAGGCTGGGCC
TTATGCCACGGGGCCTGCCAGCCACATCTCCCCCCGGGCCTGGCGGAGGCCCGACATCGAGTCCCACC
ACGTGGCCATCTCAGATGCAGAGGACTGCGTGCAGCTGAACCAGTACAAGCTGCAGAGTGAGATTGG
CAAGGGTGCCTACGGTGTGGTGAGGCTGGCCTACAACGAAAGTGAAGACAGACACTATGCAATGAAA
GTCCTTTCCAAAAAGAAGTTACTGAAGCAGTATGGCTTTCCACGTCGCCCTCCCCCGAGAGGGTCCCA
GGCTGCCCAGGGAGGACCAGCCAAGCAGCTGCTGCCCCTGGAGCGGGTGTACCAGGAGATTGCCATC
CTGAAGAAGCTGGACCACGTGAATGTGGTCAAACTGATCGAGGTCCTGGATGACCCAGCTGAGGACA
ACCTCTATTTGGTGTTTGACCTCCTGAGAAAGGGGCCCGTCATGGAAGTGCCCTGTGACAAGCCCTTC
TCGGAGGAGCAAGCTCGCCTCTACCTGCGGGACGTCATCCTGGGCCTCGAGTACTTGCACTGCCAGAA
GATCGTCCACAGGGACATCAAGCCATCCAACCTGCTCCTGGGGGATGATGGGCACGTGAAGATCGCC
GACTTTGGCGTCAGCAACCAGTTTGAGGGGAACGACGCTCAGCTGTCCAGCACGGCGGGAACCCCAG
CATTCATGGCCCCCGAGGCCATTTCTGATTCCGGCCAGAGCTTCAGTGGGAAGGCCTTGGATGTATGG
CCACTGGCCGTCACGTTGTACTGCTTTGTCTATGGGAAGTGCCCATTCATCGACGATTTCATCCTGGCC
CTCCACAGGAAGATCAAGAATGAGCCCGTGGTGTTTCCTGAGGAGCCAGAAATCAGCGAGGAGCTCA
AGGACCTGATCCTGAAGATGTTAGACAAGAATCCCGAGACGAGAATTGGGGTGCCAGACATCAAGTT
GCACCCTTGGGTGACCAAGAACGGGGAGGAGCCCCTTCCTTCGGAGGAGGAGCACTGCAGCGTGGTG
GAGGTGACAGAGGAGGAGGTTAAGAACTCAGTCAGGCTCATCCCCAGCTGGACCACGGTGATCCTGG
TGAAGTCCATGCTGAGGAAGCGTTCCTTTGGGAACCCGTTTGAGCCCCAAGCACGGAGGGAAGAGCG
ATCCATGTCTGCTCCAGGAAACCTACTGGTGAAGAAGGGTTTGGTGAAGGGGGCAAGAGCCCAGAG
CTCCCCGGCGTCCAGGAAGACGAGGCTGCATCCTGA
(SEQ ID NO: 5)

CAMKK1 T108A
protein
MEGGPAVCCQDPRAELVERVAAIDVTHLEEADGGPEPTRNGVDPPPRARAASVIPGSTSRLLPARPSLSAR
KLSLQERPAGSYLEAQAGPYATGPASHISPRAWRRPDIESHHVAISDAEDCVQLNQYKLQSEIGKGAYGVV
RLAYNESEDRHYAMKVLSKKKLLKQYGFPRRPPPRGSQAAQGGPAKQLLPLERVYQEIAILKKLDHVNVV
KLIEVLDDPAEDNLYLVFDLLRKGPVMEVPCDKPFSEEQARLYLRDVILGLEYLHCQKIVHRDIKPSNLLLG
DDGHVKIADFGVSNQFEGNDAQLSSTAGTPAFMAPEAISDSGQSFSGKALDVWATGVTLYCFVYGKCPFI
DDFILALHRKIKNEPVVFPEEPEISEELKDLILKMLDKNPETRIGVPDIKLHPWVTKNGEEPLPSEEEHCSVV
EVTEEEVKNSVRLIPSWTTVILVKSMLRKRSFGNPFEPQARREERSMSAPGNLLVKEGFGEGGKSPELPGV
QEDEAAS
(SEQ ID NO: 6)

CAMKK1 S459A nucleic
acid
ATGGAGGGGGGTCCAGCTGTCTGCTGCCAGGATCCTCGGGCAGAGCTGGTAGAACGGGTGGCAGCCA
TCGATGTGACTCACTTGGAGGAGGCAGATGGTGGCCCAGAGCCTACTAGAAACGGTGTGGACCCCCC
ACCACGGGCCAGAGCTGCCTCTGTGATCCCTGGCAGTACTTCAAGACTGCTCCCAGCCCGGCCTAGCC
TCTCAGCCAGGAAGCTTTCCCTACAGGAGCGGCCAGCAGGAAGCTATCTGGAGGCGCAGGCTGGGCC
TTATGCCACGGGGCCTGCCAGCCACATCTCCCCCCGGGCCTGGCGGAGGCCCACCATCGAGTCCCACC
ACGTGGCCATCTCAGATGCAGAGGACTGCGTGCAGCTGAACCAGTACAAGCTGCAGAGTGAGATTGG
CAAGGGTGCCTACGGTGTGGTGAGGCTGGCCTACAACGAAAGTGAAGACAGACACTATGCAATGAAA
GTCCTTTCCAAAAAGAAGTTACTGAAGCAGTATGGCTTTCCACGTCGCCCTCCCCCGAGAGGGTCCCA
GGCTGCCCAGGGAGGACCAGCCAAGCAGCTGCTGCCCCTGGAGCGGGTGTACCAGGAGATTGCCATC
CTGAAGAAGCTGGACCACGTGAATGTGGTCAAACTGATCGAGGTCCTGGATGACCCAGCTGAGGACA
ACCTCTATTTGGTGTTTGACCTCCTGAGAAAGGGGCCCGTCATGGAAGTGCCCTGTGACAAGCCCTTC
TCGGAGGAGCAAGCTCGCCTCTACCTGCGCGACGTCATCCTGGGCCTCGAGTACTTGCACTGCCAGAA
GATCGTCCACAGGGACATCAAGCCATCCAACCTGCTCCTGGGGGATGATGGGCACGTGAAGATCGCC
GACTTTGGCGTCAGCAACCAGTTTGAGGGGAACGACGCTCAGCTGTCCAGCACGGCGGGAACCCCAG
CATTCATGGCCCCCGAGGCCATTTCTGATTCCGGCCAGAGCTTCAGTGGGAAGGCCTTGGATGTATGG
GCCACTGGCCGTCACGTTGTACTGCTTTGTCTATGGGAAGTGCCCATTCATCGACGATTTCATCCTGGCC
CTCCACAGGAAGATCAAGAATGAGCCCGTGGTGTTTCCTGAGGAGCCAGAAATCAGCGAGGAGCTCA
AGGACCTGATCCTGAAGATGTTAGACAAGAATCCCGAGACGAGAATTGGGGTGCCAGACATCAAGTT
GCACCCTTGGGTGACCAAGAACGGGGAGGAGCCCCTTCCTTCGGAGGAGGAGCACTGCAGCGTGGTG
GAGGTGACAGAGGAGGAGGTTAAGAACTCAGTCAGGCTCATCCCCAGCTGGACCACGGTGATCCTGG
TGAAGTCCATGCTGAGGAAGCGTGACTTTGGGAACCCGTTTGAGCCCCAAGCACGGAGGGAAGAGCG
ATCCATGTCTGCTCCAGGAAACCTACTGGTGAAGAAGGGTTTGGTGAAGGGGGCAAGAGCCCAGAG
CTCCCCGGCGTCCAGGAAGACGAGGCTGCATCCTGA
(SEQ ID NO: 7)

CAMKK1 S459A
protein
MEGGPAVCCQDPRAELVERVAAIDVTHLEEADGGPEPTRNGVDPPPRARAASVIPGSTSRLLPARPSLSAR
KLSLQERPAGSYLEAQAGPYATGPASHISPRAWRRPTIESHHVAISDAEDCVQLNQYKLQSEIGKGAYGVV
RLAYNESEDRHYAMKVLSKKKLLKQYGFPRRPPPRGSQAAQGGPAKQLLPLERVYQEIAILKKLDHVNVV
KLIEVLDDPAEDNLYLVFDLLRKGPVMEVPCDKPFSEEQARLYLRDVILGLEYLHCQKIVHRDIKPSNLLLG
DDGHVKIADFGVSNQFEGNDAQLSSTAGTPAFMAPEAISDSGQSFSGKALDVWATGVTLYCFVYGKCPFI
DDFILALHRKIKNEPVVFPEEPEISEELKDLILKMLDKNPETRIGVPDIKLHPWVTKNGEEPLPSEEEHCSVV
EVTEEEVKNSVRLIPSWTTVILVKSMLRKRDFGNPFEPQARREERSMSAPGNLLVKEGFGEGGKSPELPGV
QEDEAAS
(SEQ ID NO: 8)

CAMKK1 T108A/S459A
nucleic acid
ATGGAGGGGGGTCCAGCTGTCTGCTGCCAGGATCCTCGGGCAGAGCTGGTAGAACGGGTGGCAGCCA
TCGATGTGACTCACTTGGAGGAGGCAGATGGTGGCCCAGAGCCTACTAGAAACGGTGTGGACCCCCC
ACCACGGGCCAGAGCTGCCTCTGTGATCCCTGGCAGTACTTCAAGACTGCTCCCAGCCCGGCCTAGCC
TCTCAGCCAGGAAGCTTTCCCTACAGGAGCGGCCAGCAGGAAGCTATCTGGAGGCGCAGGCTGGGCC
TTATGCCACGGGGCCTGCCAGCCACATCTCCCCCCGGGCCTGGCGGAGGCCCGACATCGAGTCCCACC
ACGTGGCCATCTCAGATGCAGAGGACTGCGTGCAGCTGAACCAGTACAAGCTGCAGAGTGAGATTGG
CAAGGGTGCCTACGGTGTGGTGAGGCTGGCCTACAACGAAAGTGAAGACAGACACTATGCAATGAAA TABLE 2-continued Sequences

```
                    GTCCTTTCCAAAAAGAAGTTACTGAAGCAGTATGGCTTTCCACGTCGCCCTCCCCCGAGAGGGTCCCA
                    GGCTGCCCAGGGAGGACCAGCCAAGCAGCTGCTGCCCCTGGAGCGGGTGTACCAGGAGATTGCCATC
                    CTGAAGAAGCTGGACCACGTGAATGTGGTCAAACTGATCGAGGTCCTGGATGACCCAGCTGAGGACA
                    ACCTCTATTTGGTGTTTGACCTCCTGAGAAAGGGGCCCGTCATGGAAGTGCCCTGTGACAAGCCCTTC
                    TCGGAGGAGCAAGCTCGCCTCTACCTGCGGGACGTCATCCTGGGCCTCGAGTACTTGCACTGCCAGAA
                    GATCGTCCACAGGGACATCAAGCCATCCAACCTGCTCCTGGGGGATGATGGGCACGTGAAGATCGCC
                    GACTTTGGCGTCAGCAACCAGTTTGAGGGGAACGACGCTCAGCTGTCCAGCACGGCGGGAACCCCAG
                    CATTCATGGCCCCCGAGGCCATTTCTGATTCCGGCCAGAGCTTCAGTGGGAAGGCCTTGGATGTATGG
                    GCCACTGGCGTCACGTTGTACTGCTTTGTCTATGGGAAGTGCCCATTCATCGACGATTTCATCCTGGCC
                    CTCCACAGGAAGATCAAGAATGAGCCCGTGGTGTTTCCTGAGGAGCCAGAAATCAGCGAGGAGCTCA
                    AGGACCTGATCCTGAAGATGTTAGACAAGAATCCCGAGACGAGAATTGGGGTGCCAGACATCAAGTT
                    GCACCCTTGGGTGACCAAGAACGGGGAGGAGCCCCTTCCTTCGGAGGAGGAGCACTGCAGCGTGGTG
                    GAGGTGACAGAGGAGGAGGTTAAGAACTCAGTCAGGCTCATCCCCAGCTGGACCACGGTGATCCTGG
                    TGAAGTCCATGCTGAGGAAGCGTGACTTTGGGAACCCGTTTGAGCCCCAAGCACGGAGGGAAGAGCG
                    ATCCATGTCTGCTCCAGGAAACCTACTGGTGAAGAAGGGTTTGGTGAAGGGGGCAAGAGCCCAGAG
                    CTCCCCGGCGTCCAGGAAGACGAGGCTGCATCCTGA
                    (SEQ ID NO: 9)

CAMKK1 T108A/S459A  MEGGPAVCCQDPRAELVERVAAIDVTHLEEADGGPEPTRNGVDPPPRARAASVIPGSTSRLLPARPSLSAR
protein             KLSLQERPAGSYLEAQAGPYATGPASHISPRAWRRPDIESHHVAISDAEDCVQLNQYKLQSEIGKGAYGVV
                    RLAYNESEDRHYAMKVLSKKKLLKQYGFPRRPPPRGSQAAQGGPAKQLLPLERVYQEIAILKKLDHVNVV
                    KLIEVLDDPAEDNLYLVFDLLRKGPVMEVPCDKPFSEEQARLYLRDVILGLEYLHCQKIVHRDIKPSNLLLG
                    DDGHVKIADFGVSNQFEGNDAQLSSTAGTPAFMAPEAISDSGQSFSGKALDVWATGVTLYCFVYGKCPFI
                    DDFILALHRKIKNEPVVFPEEPEISEELKDLILKMLDKNPETRIGVPDIKLHPWVTKNGEEPLPSEEEHCSVV
                    EVTEEEVKNSVRLIPSWTTVILVKSMLRKRDFGNPFEPQARREERSMSAPGNLLVKEGFGEGGKSPELPGV
                    QEDEAAS
                    (SEQ ID NO: 10)

Dab2 siRNA         GGAUUCUAUGAUGAAACUCUU
Sequence 1 (5'→3'):(SEQ ID NO: 11)
Sense Antisense           GAGUUUCAUCAUAGAAUCCTG
                    (SEQ ID NO: 12)

Dab2 siRNA         GCACCAUCAAAGAAGGAAAUU
Sequence 2 (5'→3'):(SEQ ID NO: 13)
Sense Antisense           UUUCCUUCUUUGAUGGUGCUU
                    (SEQ ID NO: 14)

Dab2 siRNA         GGUGAUGGUGUAAAAUACAUU
Sequence 3 (5'→3'):(SEQ ID NO: 15)
Sense Antisense           UGUAUUUUACACCAUCACCUU
                    (SEQ ID NO: 16)

miR145 (NR_029686)  CACCTTGTCCTCACGGTCCAGTTTTCCCAGGAATCCCTTAGATGCTAAGATGGGGATTCCTGGAAATA
                    CTGTTCTTGAGGTCATGGTT
                    (SEQ ID NO: 17)
```

Embodiments

The following list of embodiments is intended to complement, rather than displace or supersede, the previous descriptions.

Embodiment 1. A method of treating an ischemic or inflammatory condition in an organ or tissue of a patient, comprising inducing an increase of the level of CAMKK1 in said organ or tissue.

Embodiment 2. The method of embodiment 1, wherein said organ or tissue is heart, liver, kidney, brain, spine, lungs, small intestine, large intestine, arteries, joints, cartilage, skin, or any combination thereof.

Embodiment 3. The method of embodiment 2, wherein said organ or tissue is the heart or myocardium.

Embodiment 4. The method of any one of the previous embodiments, wherein the increase in the level of CAMKK1 in said organ or tissue is achieved by administering CAMKK1 protein to said organ or tissue.

Embodiment 5. The method of any one of the previous embodiments, wherein the increase in the level of CAMKK1 in said organ or tissue is achieved by administering a vector comprising a nucleic acid encoding CAMKK1 to said organ or tissue.

Embodiment 6. The method of embodiment 5, wherein the vector is a plasmid or a viral vector.

Embodiment 7. The method of any one of the previous embodiments, wherein the increase in the level of CAMKK1 in said organ or tissue is achieved by administering cells that have been modified to produce an increased level of CAMKK1.

Embodiment 8. The method of any one of the previous embodiments, wherein the increase in the level of CAMKK1 in said organ or tissue is achieved by administering conditioned media from a culture of cells that have been modified to have an increase of the level of CAMKK1.

Embodiment 9. The method of embodiment 7 or 8, wherein the cells have been modified with a vector comprising a nucleic acid encoding CAMKK1.

Embodiment 10. The method of embodiment 9, wherein the vector comprises a plasmid or a viral vector.

Embodiment 11. The method of embodiment 7 or 8, wherein the cells have been modified with an agent that induces the expression of CAMKK1.

Embodiment 12. The method of embodiment 11, wherein the agent is TGF-β, miR145, a Dab2 inhibitor, or any combination thereof.

Embodiment 13. The method of embodiment 12, wherein the Dab2 inhibitor is Dab2 siRNA.

Embodiment 14. The method of any one of the previous embodiments, wherein the CAMKK1 is a constitutively active CAMKK1.

Embodiment 15. The method of embodiment 14, wherein the constitutively active CAMKK1 comprises a CAMKK1 1-413 truncation.

Embodiment 16. The method of embodiment 14, wherein the constitutively active CAMKK1 comprises a T108A mutant CAMKK1, a S459A mutant CAMKK1, or a T108A/S459A mutant CAMKK1.

Embodiment 17. The method of any one of the previous embodiments, wherein the protein, vector, cells, or conditioned media are administered systemically, directly into the ischemic or inflamed tissue, or about the periphery of the ischemic or inflamed tissue.

Embodiment 18. The method of any one of the previous embodiments, wherein the cells are mesenchymal stem cells.

Embodiment 19. The method of any one of the previous embodiments, wherein the ischemic or inflammatory condition is acute myocardial infarction, heart failure, peripheral artery disease, stroke, liver disease, ischemic kidney disease, multiple sclerosis, traumatic brain injury, spinal cord injury, graft versus host disease (GVHD), diabetes, chronic obstructive pulmonary disease (COPD), rheumatoid arthritis, an injury from a solid organ transplant, an orthopedic injury, a cartilage disorder, a wound, or any combination thereof.

Embodiment 20. The method of any one of the previous embodiments, further comprising administering one or more additional regenerative therapies.

Embodiment 21. The method of embodiment 20, wherein the one or more regenerative therapies are mesenchymal stem cells derived from bone marrow, adipose tissue, placental tissue, umbilical cord, Wharton's Jelly, menstrual blood, stem cells, M2 macrophages, monocytes, or any combination thereof.

Embodiment 22. The method of embodiment 21, wherein the stem cells are neural progenitor cells, endothelial progenitor cells, organ specific endogenous stem cells, or any combination thereof.

Embodiment 23. The method of embodiment 22, wherein the organ specific endogenous stem cells are cardiac ckit+ cells.

What is claimed:

1. A method of preventing fibrosis or increasing vascular density in an organ or tissue of a patient, the method comprising administering to the patient:
 (a) cells comprising:
  a vector comprising a nucleic acid encoding human calcium/calmodulin-dependent protein kinase kinase 1 (CAMKK1) selected from the group of: the protein of SEQ ID NO: 4, the T108A mutant CAMKK1, the S459A mutant CAMKK1, or the T108A/S459A mutant CAMKK1, wherein T108 corresponds to position 108 of SEQ ID NO: 2 and S459 corresponds to position 458 of SEQ ID NO: 2, to said organ or tissue, and optionally wherein the vector is a plasmid or a viral vector; or
 (b) conditioned media from a culture of the cells of (a) that have been modified to have an increase of the level of human CAMKK1 protein to said organ or tissue, thereby preventing fibrosis or increasing vascular density in the organ or tissue of the patient.

2. The method of claim 1, wherein said organ or tissue is heart, myocardium, liver, kidney, brain, spine, lungs, small intestine, large intestine, arteries, joints, cartilage, skin, or any combination thereof.

3. The method of claim 1, wherein the cells have been modified with the vector comprising the nucleic acid encoding human CAMKK1 to express an elevated level of human CAMKK1.

4. The method of claim 1, wherein the cells or conditioned media are administered systemically, directly into said organ or tissue, or about the periphery of said organ or tissue, wherein said organ or tissue is inflamed or damaged.

5. The method of claim 1, wherein the cells are mesenchymal stem cells.

6. The method of claim 1, further comprising administering one or more additional regenerative therapies.

7. The method of claim 6, wherein the one or more regenerative therapies comprise administering mesenchymal stem cells derived from bone marrow, adipose tissue, placental tissue, umbilical cord, Wharton's Jelly, menstrual blood, stem cells, M2 macrophages, monocytes, or any combination thereof.

8. The method of claim 7, wherein the stem cells are neural progenitor cells, endothelial progenitor cells, organ specific endogenous stem cells, or any combination thereof.

9. The method of claim 8, wherein the organ specific endogenous stem cells are cardiac ckit+cells.

10. The method of claim 1, wherein the organ or tissue is heart or myocardium.

11. The method of claim 10, wherein the heart or myocardium is associated with a condition of heart failure or stroke, wherein the heart failure is with or without ejection fraction.

12. A method of preventing fibrosis or increasing vascular density in an organ or tissue of a patient by modulating a secretome expression of a cell in said organ or tissue by human CAMKK1, the method comprising:
 administering a vector comprising a nucleic acid encoding human calcium/calmodulin-dependent protein kinase kinase 1 (CAMKK1) selected from the group of: the protein of SEQ ID NO: 4, the T108A mutant CAMKKI, the S459A mutant CAMKK, or the T108A/S459A mutant CAMKKI, wherein T108 corresponds to position 108 of SEQ ID NO: 2 and S459 corresponds to position 458 of SEQ ID NO: 2, to a cell of said organ or tissue thereby inducing an increased level of human CAMKK1 in the cell, and optionally wherein the vector is a plasmid or a viral vector,
 thereby modulating a secretome expression of the cell by the human CAMKK1 to prevent fibrosis or increase vascular density in the organ or tissue in the patient.

13. The method of claim 12, wherein said organ or tissue is heart, myocardium, liver, kidney, brain, spine, lungs, small intestine, large intestine, arteries, joints, cartilage, skin, or any combination thereof.

14. The method of claim 12, wherein the organ or tissue is heart or myocardium.

\* \* \* \* \*

UNITED STATES PATENT AND TRADEMARK OFFICE
CERTIFICATE OF CORRECTION

PATENT NO. : 11,273,208 B2
APPLICATION NO. : 15/610540
DATED : March 15, 2022
INVENTOR(S) : Marc S. Penn, Matthew Kiedrowski and Maritza Mayorga It is certified that error appears in the above-identified patent and that said Letters Patent is hereby corrected as shown below:

In the Claims

<u>Column 44, Line 23, Claim 12 should be replaced with the following:</u>
12. A method of preventing fibrosis or increasing vascular density in an organ or tissue of a patient by modulating a secretome expression of a cell in said organ or tissue by human CAMKK1, the method comprising:
    administering a vector comprising a nucleic acid encoding human calcium/calmodulin-dependent protein kinase kinase 1 (CAMKK1) selected from the group of: the protein of SEQ ID NO: 4, the T108A mutant CAMKK1, the S459A mutant CAMKK1, or the T108A/S459A mutant CAMKK1, wherein T108 corresponds to position 108 of SEQ ID NO: 2 and S459 corresponds to position 458 of SEQ ID NO: 2, to a cell of said organ or tissue thereby inducing an increased level of human CAMKK1 in the cell, and optionally wherein the vector is a plasmid or a viral vector,
    thereby modulating a secretome expression of the cell by the human CAMKK1 to prevent fibrosis or increase vascular density in the organ or tissue in the patient.

Signed and Sealed this
Second Day of August, 2022

Katherine Kelly Vidal
*Director of the United States Patent and Trademark Office*

SEQUENCE LISTING

```
<160> NUMBER OF SEQ ID NOS: 17

<210> SEQ ID NO 1
<211> LENGTH: 1518
<212> TYPE: DNA
<213> ORGANISM: Homo sapiens

<400> SEQUENCE: 1 atggagggg  gtccagctgt  ctgctgccag  gatcctcggg  cagagctggt  agaacgggtg      60
gcagccatcg  atgtgactca  cttggaggag  gcagatggtg  gcccagagcc  tactagaaac     120
ggtgtggacc  ccccaccacg  ggccagagct  gcctctgtga  tccctggcag  tacttcaaga     180
ctgctcccag  cccggcctag  cctctcagcc  aggaagcttt  ccctacagga  gcggccagca     240
ggaagctatc  tggaggcgca  ggctgggcct  tatgccacgg  ggcctgccag  ccacatctcc     300
ccccgggcct  ggcggaggcc  caccatcgag  tcccaccacg  tggccatctc  agatgcagag     360
gactgcgtgc  agctgaacca  gtacaagctg  cagagtgaga  ttggcaaggg  tgcctacggt     420
gtggtgaggc  tggcctacaa  cgaaagtgaa  gacagacact  atgcaatgaa  agtcctttcc     480
aaaaagaagt  tactgaagca  gtatggcttt  ccacgtcgcc  ctcccccgag  agggtcccag     540
gctgcccagg  gaggaccagc  caagcagctg  ctgcccctgg  agcgggtgta  ccaggagatt     600
gccatcctga  agaagctgga  ccacgtgaat  gtggtcaaac  tgatcgaggt  cctggatgac     660
ccagctgagg  acaacctcta  tttggtgttt  gacctcctga  gaaagggggcc  cgtcatggaa     720 gtgccctgtg  acaagcccct  tctcggaggag  caagctcgcc  tctacctgcg  ggacgtcatc     780
ctgggcctcg  agtacttgca  ctgccagaag  atcgtccaca  gggacatcaa  gccatccaac     840
ctgctcctgg  gggatgatgg  gcacgtgaag  atcgccgact  ttggcgtcag  caaccagttt     900
gaggggaacg  acgctcagct  gtccagcacg  gcgggaaccc  cagcattcat  ggcccccgag     960
gccatttctg  attccggcca  gagcttcagt  gggaaggcct  tggatgtatg  ggccactggc    1020
gtcacgttgt  actgctttgt  ctatgggaag  tgcccattca  tcgacgattt  catcctggcc    1080
```

```
ctccacagga agatcaagaa tgagcccgtg gtgtttcctg aggagccaga aatcagcgag   1140
gagctcaagg acctgatcct gaagatgtta gacaagaatc ccgagacgag aattggggtg   1200
ccagacatca agttgcaccc ttgggtgacc aagaacgggg aggagcccct tccttcggag   1260
gaggagcact gcagcgtggt ggaggtgaca gaggaggagg ttaagaactc agtcaggctc   1320
atccccagct ggaccacggt gatcctggtg aagtccatgc tgaggaagcg ttcctttggg   1380
aacccgtttg agccccaagc acggagggaa gagcgatcca tgtctgctcc aggaaaccta   1440
ctggtgaaag aagggtttgg tgaaggggc aagagcccag agctccccgg cgtccaggaa   1500
gacgaggctg catcctga                                                 1518
```

<210> SEQ ID NO 2
<211> LENGTH: 505
<212> TYPE: PRT
<213> ORGANISM: Homo sapiens

<400> SEQUENCE: 2

```
Met Glu Gly Gly Pro Ala Val Cys Cys Gln Asp Pro Arg Ala Glu Leu
1               5                   10                  15

Val Glu Arg Val Ala Ala Ile Asp Val Thr His Leu Glu Glu Ala Asp
            20                  25                  30

Gly Gly Pro Glu Pro Thr Arg Asn Gly Val Asp Pro Pro Arg Ala
        35                  40                  45

Arg Ala Ala Ser Val Ile Pro Gly Ser Thr Ser Arg Leu Leu Pro Ala
    50                  55                  60

Arg Pro Ser Leu Ser Ala Arg Lys Leu Ser Leu Gln Glu Arg Pro Ala
65                  70                  75                  80

Gly Ser Tyr Leu Glu Ala Gln Ala Gly Pro Tyr Ala Thr Gly Pro Ala
                85                  90                  95

Ser His Ile Ser Pro Arg Ala Trp Arg Arg Pro Thr Ile Glu Ser His
            100                 105                 110

His Val Ala Ile Ser Asp Ala Glu Asp Cys Val Gln Leu Asn Gln Tyr
        115                 120                 125

Lys Leu Gln Ser Glu Ile Gly Lys Gly Ala Tyr Gly Val Val Arg Leu
    130                 135                 140

Ala Tyr Asn Glu Ser Glu Asp Arg His Tyr Ala Met Lys Val Leu Ser
145                 150                 155                 160

Lys Lys Lys Leu Leu Lys Gln Tyr Gly Phe Pro Arg Arg Pro Pro Pro
                165                 170                 175

Arg Gly Ser Gln Ala Ala Gln Gly Gly Pro Ala Lys Gln Leu Leu Pro
            180                 185                 190

Leu Glu Arg Val Tyr Gln Glu Ile Ala Ile Leu Lys Lys Leu Asp His
        195                 200                 205

Val Asn Val Val Lys Leu Ile Glu Val Leu Asp Asp Pro Ala Glu Asp
    210                 215                 220

Asn Leu Tyr Leu Val Phe Asp Leu Leu Arg Lys Gly Pro Val Met Glu
225                 230                 235                 240

Val Pro Cys Asp Lys Pro Phe Ser Glu Glu Gln Ala Arg Leu Tyr Leu
                245                 250                 255

Arg Asp Val Ile Leu Gly Leu Glu Tyr Leu His Cys Gln Lys Ile Val
            260                 265                 270

His Arg Asp Ile Lys Pro Ser Asn Leu Leu Leu Gly Asp Asp Gly His
        275                 280                 285
```

```
Val Lys Ile Ala Asp Phe Gly Val Ser Asn Gln Phe Glu Gly Asn Asp
    290                 295                 300

Ala Gln Leu Ser Ser Thr Ala Gly Thr Pro Ala Phe Met Ala Pro Glu
305                 310                 315                 320

Ala Ile Ser Asp Ser Gly Gln Ser Phe Ser Gly Lys Ala Leu Asp Val
                325                 330                 335

Trp Ala Thr Gly Val Thr Leu Tyr Cys Phe Val Tyr Gly Lys Cys Pro
                340                 345                 350

Phe Ile Asp Asp Phe Ile Leu Ala Leu His Arg Lys Ile Lys Asn Glu
            355                 360                 365

Pro Val Val Phe Pro Glu Glu Pro Glu Ile Ser Glu Glu Leu Lys Asp
370                 375                 380

Leu Ile Leu Lys Met Leu Asp Lys Asn Pro Glu Thr Arg Ile Gly Val
385                 390                 395                 400

Pro Asp Ile Lys Leu His Pro Trp Val Thr Lys Asn Gly Glu Glu Pro
                405                 410                 415

Leu Pro Ser Glu Glu Glu His Cys Ser Val Val Glu Val Thr Glu Glu
                420                 425                 430

Glu Val Lys Asn Ser Val Arg Leu Ile Pro Ser Trp Thr Thr Val Ile
            435                 440                 445

Leu Val Lys Ser Met Leu Arg Lys Arg Ser Phe Gly Asn Pro Phe Glu
450                 455                 460

Pro Gln Ala Arg Arg Glu Glu Arg Ser Met Ser Ala Pro Gly Asn Leu
465                 470                 475                 480

Leu Val Lys Glu Gly Phe Gly Glu Gly Gly Lys Ser Pro Glu Leu Pro
                485                 490                 495

Gly Val Gln Glu Asp Glu Ala Ala Ser
                500                 505

<210> SEQ ID NO 3
<211> LENGTH: 1242
<212> TYPE: DNA
<213> ORGANISM: Homo sapiens

<400> SEQUENCE: 3 atggagggg gtccagctgt ctgctgccag gatcctcggg cagagctggt agaacgggtg        60
gcagccatcg atgtgactca cttggaggag gcagatggtg gcccagagcc tactagaaac       120
ggtgtggacc cccaccacg ggccagagct gcctctgtga tccctggcag tacttcaaga        180
ctgctcccag cccggcctag cctctcagcc aggaagcttt ccctacagga gcggccagca       240
ggaagctatc tggaggcgca ggctgggcct tatgccacgg ggcctgccag ccacatctcc       300
ccccgggcct ggcggaggcc caccatcgag tcccaccacg tggccatctc agatgcagag       360
gactgcgtgc agctgaacca gtacaagctg cagagtgaga ttggcaaggg tgcctacggt       420
gtggtgaggc tggcctacaa cgaaagtgaa gacagacact atgcaatgaa agtcctttcc       480
aaaaagaagt tactgaagca gtatggcttt ccacgtcgcc ctcccccgag agggtcccag       540
gctgcccagg aggaccagcc aagcagctg ctgcccctgg agcgggtgta ccaggagatt       600
gccatcctga gaagctgga ccacgtgaat gtggtcaaac tgatcgaggt cctggatgac       660
ccagctgagg acaacctcta tttggtgttt gacctcctga aaaggggcc cgtcatggaa       720 gtgccctgtg acaagccctt ctcggaggag caagctcgcc tctacctgcg ggacgtcatc       780
ctgggcctcg agtacttgca ctgccagaag atcgtccaca gggacatcaa gccatccaac       840
ctgctcctgg gggatgatgg gcacgtgaag atcgccgact ttggcgtcag caaccagttt       900
```

```
gaggggaacg acgctcagct gtccagcacg gcgggaaccc cagcattcat ggcccccgag    960
gccatttctg attccggcca gagcttcagt gggaaggcct tggatgtatg gccactggc   1020 gtcacgttgt actgctttgt ctatgggaag tgcccattca tcgacgattt catcctggcc  1080
ctccacagga gatcaagaa tgagcccgtg gtgtttcctg aggagccaga atcagcgag    1140 gagctcaagg acctgatcct gaagatgtta gacaagaatc ccgagacgag aattggggtg  1200
ccagacatca agttgcaccc ttgggtgacc aagaacgggt ga                     1242
```

<210> SEQ ID NO 4
<211> LENGTH: 413
<212> TYPE: PRT
<213> ORGANISM: Homo sapiens

<400> SEQUENCE: 4

```
Met Glu Gly Gly Pro Ala Val Cys Cys Gln Asp Pro Arg Ala Glu Leu
 1               5                  10                  15

Val Glu Arg Val Ala Ala Ile Asp Val Thr His Leu Glu Glu Ala Asp
            20                  25                  30

Gly Gly Pro Glu Pro Thr Arg Asn Gly Val Asp Pro Pro Arg Ala
        35                  40                  45

Arg Ala Ala Ser Val Ile Pro Gly Ser Thr Ser Arg Leu Leu Pro Ala
    50                  55                  60

Arg Pro Ser Leu Ser Ala Arg Lys Leu Ser Leu Gln Glu Arg Pro Ala
65                  70                  75                  80

Gly Ser Tyr Leu Glu Ala Gln Ala Gly Pro Tyr Ala Thr Gly Pro Ala
                85                  90                  95

Ser His Ile Ser Pro Arg Ala Trp Arg Arg Pro Thr Ile Glu Ser His
            100                 105                 110

His Val Ala Ile Ser Asp Ala Glu Asp Cys Val Gln Leu Asn Gln Tyr
        115                 120                 125

Lys Leu Gln Ser Glu Ile Gly Lys Gly Ala Tyr Gly Val Val Arg Leu
    130                 135                 140

Ala Tyr Asn Glu Ser Glu Asp Arg His Tyr Ala Met Lys Val Leu Ser
145                 150                 155                 160

Lys Lys Lys Leu Leu Lys Gln Tyr Gly Phe Pro Arg Arg Pro Pro Pro
                165                 170                 175

Arg Gly Ser Gln Ala Ala Gln Gly Gly Pro Ala Lys Gln Leu Leu Pro
            180                 185                 190

Leu Glu Arg Val Tyr Gln Glu Ile Ala Ile Leu Lys Lys Leu Asp His
        195                 200                 205

Val Asn Val Val Lys Leu Ile Glu Val Leu Asp Asp Pro Ala Glu Asp
    210                 215                 220

Asn Leu Tyr Leu Val Phe Asp Leu Leu Arg Lys Gly Pro Val Met Glu
225                 230                 235                 240

Val Pro Cys Asp Lys Pro Phe Ser Glu Glu Gln Ala Arg Leu Tyr Leu
                245                 250                 255

Arg Asp Val Ile Leu Gly Leu Glu Tyr Leu His Cys Gln Lys Ile Val
            260                 265                 270

His Arg Asp Ile Lys Pro Ser Asn Leu Leu Leu Gly Asp Asp Gly His
        275                 280                 285

Val Lys Ile Ala Asp Phe Gly Val Ser Asn Gln Phe Glu Gly Asn Asp
    290                 295                 300

Ala Gln Leu Ser Ser Thr Ala Gly Thr Pro Ala Phe Met Ala Pro Glu
```

```
                305                 310                 315                 320
Ala Ile Ser Asp Ser Gly Gln Ser Phe Ser Gly Lys Ala Leu Asp Val
                    325                 330                 335

Trp Ala Thr Gly Val Thr Leu Tyr Cys Phe Val Tyr Gly Lys Cys Pro
                340                 345                 350

Phe Ile Asp Asp Phe Ile Leu Ala Leu His Arg Lys Ile Lys Asn Glu
                355                 360                 365

Pro Val Val Phe Pro Glu Glu Pro Ile Ser Glu Glu Leu Lys Asp
        370                 375                 380

Leu Ile Leu Lys Met Leu Asp Lys Asn Pro Glu Thr Arg Ile Gly Val
385                 390                 395                 400

Pro Asp Ile Lys Leu His Pro Trp Val Thr Lys Asn Gly
                405                 410

<210> SEQ ID NO 5
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggaggggg gtccagctgt ctgctgccag gatcctcggg cagagctggt agaacgggtg      60
gcagccatcg atgtgactca cttggaggag gcagatggtg gcccagagcc tactagaaac     120
ggtgtggacc ccccaccacg ggccagagct gcctctgtga tccctggcag tacttcaaga     180
ctgctcccag cccggcctag cctctcagcc aggaagcttt ccctacagga gcggccagca     240
ggaagctatc tggaggcgca ggctgggcct tatgccacgg ggcctgccag ccacatctcc     300
ccccgggcct ggcggaggcc cgacatcgag tcccaccacg tggccatctc agatgcagag     360
gactgcgtgc agctgaacca gtacaagctg cagagtgaga ttggcaaggg tgcctacggt     420
gtggtgaggc tggcctacaa cgaaagtgaa gacagacact atgcaatgaa agtcctttcc     480
aaaaagaagt tactgaagca gtatggcttt ccacgtcgcc ctcccccgag agggtcccag     540
gctgcccagg gaggaccagc caagcagctg ctgcccctgg agcgggtgta ccaggagatt     600
gccatcctga gaagctgga ccacgtgaat gtggtcaaac tgatcgaggt cctggatgac     660
ccagctgagg acaacctcta tttggtgttt gacctcctga aaagggggcc cgtcatggaa     720
gtgccctgtg acaagccctt ctcggaggag caagctcgcc tctacctgcg ggacgtcatc     780
ctgggcctcg agtacttgca ctgccagaag atcgtccaca gggacatcaa gccatccaac     840
ctgctcctgg gggatgatgg gcacgtgaag atcgccgact tggcgtcag caaccagttt     900 gaggggaacg acgctcagct gtccagcacg gcgggaaccc cagcattcat ggccccgag     960 gccatttctg attccggcca gagcttcagt gggaaggcct ggatgtatg gccactggc    1020 gtcacgttgt actgctttgt ctatgggaag tgcccattca tcgacgattt catcctggcc    1080
ctccacagga agatcaagaa tgagcccgtg gtgttcctg aggagccaga aatcagcgag    1140
gagctcaagg acctgatcct gaagatgtta gacaagaatc ccgagacgag aattggggtg    1200
ccagacatca agttgcaccc ttgggtgacc aagaacgggg aggagcccct tccttcggag    1260
gaggagcact gcagcgtggt ggaggtgaca gaggaggagg ttaagaactc agtcaggctc    1320
atccccagct ggaccacggt gatcctggtg aagtccatgc tgaggaagcg ttcctttggg    1380
aacccgtttg agccccaagc acggagggaa gagcgatcca tgtctgctcc aggaaaccta    1440
```

```
ctggtgaaag aagggtttgg tgaaggggc aagagcccag agctccccgg cgtccaggaa    1500
gacgaggctg catcctga                                                  1518
```

<210> SEQ ID NO 6
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Glu Gly Gly Pro Ala Val Cys Cys Gln Asp Pro Arg Ala Glu Leu
1               5                   10                  15

Val Glu Arg Val Ala Ala Ile Asp Val Thr His Leu Glu Glu Ala Asp
            20                  25                  30

Gly Gly Pro Glu Pro Thr Arg Asn Gly Val Asp Pro Pro Arg Ala
        35                  40                  45

Arg Ala Ser Val Ile Pro Gly Ser Thr Ser Arg Leu Leu Pro Ala
50                  55                  60

Arg Pro Ser Leu Ser Ala Arg Lys Leu Ser Leu Gln Glu Arg Pro Ala
65                  70                  75                  80

Gly Ser Tyr Leu Glu Ala Gln Ala Gly Pro Tyr Ala Thr Gly Pro Ala
                85                  90                  95

Ser His Ile Ser Pro Arg Ala Trp Arg Pro Asp Ile Glu Ser His
            100                 105                 110

His Val Ala Ile Ser Asp Ala Glu Asp Cys Val Gln Leu Asn Gln Tyr
        115                 120                 125

Lys Leu Gln Ser Glu Ile Gly Lys Gly Ala Tyr Gly Val Val Arg Leu
130                 135                 140

Ala Tyr Asn Glu Ser Glu Asp Arg His Tyr Ala Met Lys Val Leu Ser
145                 150                 155                 160

Lys Lys Lys Leu Leu Lys Gln Tyr Gly Phe Pro Arg Arg Pro Pro
                165                 170                 175

Arg Gly Ser Gln Ala Ala Gln Gly Gly Pro Ala Lys Gln Leu Leu Pro
            180                 185                 190

Leu Glu Arg Val Tyr Gln Glu Ile Ala Ile Leu Lys Lys Leu Asp His
        195                 200                 205

Val Asn Val Val Lys Leu Ile Glu Val Leu Asp Asp Pro Ala Glu Asp
210                 215                 220

Asn Leu Tyr Leu Val Phe Asp Leu Leu Arg Lys Gly Pro Val Met Glu
225                 230                 235                 240

Val Pro Cys Asp Lys Pro Phe Ser Glu Glu Gln Ala Arg Leu Tyr Leu
                245                 250                 255

Arg Asp Val Ile Leu Gly Leu Glu Tyr Leu His Cys Gln Lys Ile Val
            260                 265                 270

His Arg Asp Ile Lys Pro Ser Asn Leu Leu Gly Asp Asp Gly His
        275                 280                 285

Val Lys Ile Ala Asp Phe Gly Val Ser Asn Gln Phe Glu Gly Asn Asp
290                 295                 300

Ala Gln Leu Ser Ser Thr Ala Gly Thr Pro Ala Phe Met Ala Pro Glu
305                 310                 315                 320

Ala Ile Ser Asp Ser Gly Gln Ser Phe Ser Gly Lys Ala Leu Asp Val
                325                 330                 335

Trp Ala Thr Gly Val Thr Leu Tyr Cys Phe Val Tyr Gly Lys Cys Pro
```

```
                    340                 345                 350
Phe Ile Asp Asp Phe Ile Leu Ala Leu His Arg Lys Ile Lys Asn Glu
            355                 360                 365

Pro Val Val Phe Pro Glu Glu Pro Glu Ile Ser Glu Glu Leu Lys Asp
        370                 375                 380

Leu Ile Leu Lys Met Leu Asp Lys Asn Pro Glu Thr Arg Ile Gly Val
385                 390                 395                 400

Pro Asp Ile Lys Leu His Pro Trp Val Thr Lys Asn Gly Glu Glu Pro
                405                 410                 415

Leu Pro Ser Glu Glu Glu His Cys Ser Val Val Glu Val Thr Glu Glu
            420                 425                 430

Glu Val Lys Asn Ser Val Arg Leu Ile Pro Ser Trp Thr Thr Val Ile
        435                 440                 445

Leu Val Lys Ser Met Leu Arg Lys Arg Ser Phe Gly Asn Pro Phe Glu
    450                 455                 460

Pro Gln Ala Arg Arg Glu Glu Arg Ser Met Ser Ala Pro Gly Asn Leu
465                 470                 475                 480

Leu Val Lys Glu Gly Phe Gly Glu Gly Gly Lys Ser Pro Glu Leu Pro
                485                 490                 495

Gly Val Gln Glu Asp Glu Ala Ala Ser
            500                 505

<210> SEQ ID NO 7
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggaggggg gtccagctgt ctgctgccag gatcctcggg cagagctggt agaacgggtg      60
gcagccatcg atgtgactca cttggaggag gcagatggtg gcccagagcc tactagaaac     120
ggtgtggacc ccccaccacg ggccagagct gcctctgtga tccctggcag tacttcaaga     180
ctgctcccag cccggcctag cctctcagcc aggaagcttt ccctacagga gcggccagca     240
ggaagctatc tggaggcgca ggctgggcct tatgccacgg gcctgccag ccacatctcc      300 ccccgggcct ggcggaggcc caccatcgag tcccaccacg tggccatctc agatgcagag     360
gactgcgtgc agctgaacca gtacaagctg cagagtgaga ttggcaaggg tgcctacggt     420
gtggtgaggc tggcctacaa cgaaagtgaa gacagacact atgcaatgaa gtccttttcc     480
aaaaagaagt tactgaagca gtatggcttt ccacgtcgcc ctccccgag agggtcccag      540 gctgcccagg gaggaccagc caagcagctg ctgcccctgg agcgggtgta ccaggagatt     600
gccatcctga agaagctgga ccacgtgaat gtggtcaaac tgatcgaggt cctggatgac     660
ccagctgagg acaacctcta tttggtgttt gacctcctga aagggggcc cgtcatggaa     720 gtgccctgtg acaagccctt ctcggaggag caagctcgcc tctacctgcg ggacgtcatc     780
ctgggcctcg agtacttgca ctgccagaag atcgtccaca gggacatcaa gccatccaac     840
ctgctcctgg gggatgatgg gcacgtgaag atcgccgact ttggcgtcag caaccagttt     900
gaggggaacg acgctcagct gtccagcacg gcgggaaccc cagcattcat ggccccccgag    960 gccatttctg attccggcca gagcttcagt gggaaggcct tggatgtatg gccactggc    1020 gtcacgttgt actgctttgt ctatgggaag tgcccattca tcgacgattt catcctggcc    1080
```

```
ctccacagga agatcaagaa tgagcccgtg gtgtttcctg aggagccaga atcagcgag       1140 gagctcaagg acctgatcct gaagatgtta cacaagaatc ccgagacgag aattggggtg      1200
ccagacatca agttgcaccc ttgggtgacc aagaacgggg aggagcccct tccttcggag      1260
gaggagcact gcagcgtggt ggaggtgaca gaggaggagg ttaagaactc agtcaggctc      1320
atccccagct ggaccacggt gatcctggtg aagtccatgc tgaggaagcg tgactttggg      1380
aacccgtttg agccccaagc acggagggaa gagcgatcca tgtctgctcc aggaaaccta      1440
ctggtgaaag aagggtttgg tgaaggggggc aagagcccag agctccccgg cgtccaggaa    1500
gacgaggctg catcctga                                                   1518
```

<210> SEQ ID NO 8
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Glu Gly Gly Pro Ala Val Cys Cys Gln Asp Pro Arg Ala Glu Leu
1               5                   10                  15

Val Glu Arg Val Ala Ala Ile Asp Val Thr His Leu Glu Glu Ala Asp
                20                  25                  30

Gly Gly Pro Glu Pro Thr Arg Asn Gly Val Asp Pro Pro Arg Ala
            35                  40                  45

Arg Ala Ala Ser Val Ile Pro Gly Ser Thr Ser Arg Leu Leu Pro Ala
    50                  55                  60

Arg Pro Ser Leu Ser Ala Arg Lys Leu Ser Leu Gln Glu Arg Pro Ala
65                  70                  75                  80

Gly Ser Tyr Leu Glu Ala Gln Ala Gly Pro Tyr Ala Thr Gly Pro Ala
                85                  90                  95

Ser His Ile Ser Pro Arg Ala Trp Arg Arg Pro Thr Ile Glu Ser His
            100                 105                 110

His Val Ala Ile Ser Asp Ala Glu Asp Cys Val Gln Leu Asn Gln Tyr
        115                 120                 125

Lys Leu Gln Ser Glu Ile Gly Lys Gly Ala Tyr Gly Val Val Arg Leu
    130                 135                 140

Ala Tyr Asn Glu Ser Glu Asp Arg His Tyr Ala Met Lys Val Leu Ser
145                 150                 155                 160

Lys Lys Lys Leu Leu Lys Gln Tyr Gly Phe Pro Arg Arg Pro Pro Pro
                165                 170                 175

Arg Gly Ser Gln Ala Ala Gln Gly Gly Pro Ala Lys Gln Leu Leu Pro
            180                 185                 190

Leu Glu Arg Val Tyr Gln Glu Ile Ala Ile Leu Lys Lys Leu Asp His
        195                 200                 205

Val Asn Val Val Lys Leu Ile Glu Val Leu Asp Asp Pro Ala Glu Asp
    210                 215                 220

Asn Leu Tyr Leu Val Phe Asp Leu Leu Arg Lys Gly Pro Val Met Glu
225                 230                 235                 240

Val Pro Cys Asp Lys Pro Phe Ser Glu Glu Gln Ala Arg Leu Tyr Leu
                245                 250                 255

Arg Asp Val Ile Leu Gly Leu Glu Tyr Leu His Cys Gln Lys Ile Val
            260                 265                 270

His Arg Asp Ile Lys Pro Ser Asn Leu Leu Leu Gly Asp Asp Gly His
```

```
                275                 280                 285
Val Lys Ile Ala Asp Phe Gly Val Ser Asn Gln Phe Glu Gly Asn Asp
            290                 295                 300
Ala Gln Leu Ser Ser Thr Ala Gly Thr Pro Ala Phe Met Ala Pro Glu
305                 310                 315                 320
Ala Ile Ser Asp Ser Gly Gln Ser Phe Ser Gly Lys Ala Leu Asp Val
                325                 330                 335
Trp Ala Thr Gly Val Thr Leu Tyr Cys Phe Val Tyr Gly Lys Cys Pro
            340                 345                 350
Phe Ile Asp Asp Phe Ile Leu Ala Leu His Arg Lys Ile Lys Asn Glu
                355                 360                 365
Pro Val Val Phe Pro Glu Glu Pro Glu Ile Ser Glu Glu Leu Lys Asp
            370                 375                 380
Leu Ile Leu Lys Met Leu Asp Lys Asn Pro Glu Thr Arg Ile Gly Val
385                 390                 395                 400
Pro Asp Ile Lys Leu His Pro Trp Val Thr Lys Asn Gly Glu Glu Pro
                405                 410                 415
Leu Pro Ser Glu Glu Glu His Cys Ser Val Val Glu Val Thr Glu Glu
            420                 425                 430
Glu Val Lys Asn Ser Val Arg Leu Ile Pro Ser Trp Thr Thr Val Ile
                435                 440                 445
Leu Val Lys Ser Met Leu Arg Lys Arg Asp Phe Gly Asn Pro Phe Glu
            450                 455                 460
Pro Gln Ala Arg Arg Glu Glu Arg Ser Met Ser Ala Pro Gly Asn Leu
465                 470                 475                 480
Leu Val Lys Glu Gly Phe Gly Glu Gly Gly Lys Ser Pro Glu Leu Pro
                485                 490                 495
Gly Val Gln Glu Asp Glu Ala Ala Ser
            500                 505

<210> SEQ ID NO 9
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9 atggagggg  gtccagctgt  ctgctgccag  gatcctcggg  cagagctggt  agaacgggtg      60
gcagccatcg  atgtgactca  cttggaggag  gcagatggtg  gcccagagcc  tactagaaac     120
ggtgtggacc  ccccaccacg  ggccagagct  gcctctgtga  tccctggcag  tacttcaaga     180
ctgctcccag  cccggcctag  cctctcagcc  aggaagcttt  ccctacagga  gcggccagca     240
ggaagctatc  tggaggcgca  ggctgggcct  tatgccacgg  ggcctgccag  ccacatctcc     300
ccccgggcct  gcggaggcc  cgacatcgag  tcccaccacg  tggccatctc  agatgcagag     360
gactgcgtgc  agctgaacca  gtacaagctg  cagagtgaga  ttggcaaggg  tgcctacggt     420
gtggtgaggc  tggcctacaa  cgaaagtgaa  gacagacact  atgcaatgaa  agtcctttcc     480
aaaaagaagt  tactgaagca  gtatggcttt  ccacgtcgcc  ctcccccgag  agggtcccag     540
gctgcccagg  gaggaccagc  caagcagctg  ctgcccctgg  agcgggtgta  ccaggagatt     600
gccatcctga  agaagctgga  ccacgtgaat  gtggtcaaac  tgatcgaggt  cctggatgac     660
ccagctgagg  acaacctcta  tttggtgttt  gacctcctga  gaaggggggcc  cgtcatggaa     720
```

```
gtgccctgtg acaagccctt ctcggaggag caagctcgcc tctacctgcg ggacgtcatc    780
ctgggcctcg agtacttgca ctgccagaag atcgtccaca gggacatcaa gccatccaac    840
ctgctcctgg gggatgatgg gcacgtgaag atcgccgact ttggcgtcag caaccagttt    900
gaggggaacg acgctcagct gtccagcacg gcgggaaccc cagcattcat ggcccccgag    960
gccatttctg attccggcca gagcttcagt gggaaggcct tggatgtatg ggccactggc   1020
gtcacgttgt actgctttgt ctatgggaag tgcccattca tcgacgattt catcctggcc   1080
ctccacagga agatcaagaa tgagcccgtg gtgtttcctg aggagccaga aatcagcgag   1140
gagctcaagg acctgatcct gaagatgtta gacaagaatc ccgagacgag aattggggtg   1200
ccagacatca agttgcaccc ttgggtgacc aagaacgggg aggagcccct tccttcggag   1260
gaggagcact gcagcgtggt ggaggtgaca gaggaggagg ttaagaactc agtcaggctc   1320
atccccagct ggaccacggt gatcctggtg aagtccatgc tgaggaagcg tgactttggg   1380
aacccgtttg agcccaagc acggagggaa gagcgatcca tgtctgctcc aggaaaccta   1440
ctggtgaaag aagggtttgg tgaaggggc aagagcccag agctccccgg cgtccaggaa   1500
gacgaggctg catcctga                                                  1518
```

<210> SEQ ID NO 10
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Gly Gly Pro Ala Val Cys Cys Gln Asp Pro Arg Ala Glu Leu
1               5                   10                  15

Val Glu Arg Val Ala Ala Ile Asp Val Thr His Leu Glu Glu Ala Asp
                20                  25                  30

Gly Gly Pro Glu Pro Thr Arg Asn Gly Val Asp Pro Pro Arg Ala
            35                  40                  45

Arg Ala Ala Ser Val Ile Pro Gly Ser Thr Ser Arg Leu Leu Pro Ala
        50                  55                  60

Arg Pro Ser Leu Ser Ala Arg Lys Leu Ser Leu Gln Glu Arg Pro Ala
65                  70                  75                  80

Gly Ser Tyr Leu Glu Ala Gln Ala Gly Pro Tyr Ala Thr Gly Pro Ala
                85                  90                  95

Ser His Ile Ser Pro Arg Ala Trp Arg Arg Pro Asp Ile Glu Ser His
            100                 105                 110

His Val Ala Ile Ser Asp Ala Glu Asp Cys Val Gln Leu Asn Gln Tyr
        115                 120                 125

Lys Leu Gln Ser Glu Ile Gly Lys Gly Ala Tyr Gly Val Val Arg Leu
    130                 135                 140

Ala Tyr Asn Glu Ser Glu Asp Arg His Tyr Ala Met Lys Val Leu Ser
145                 150                 155                 160

Lys Lys Lys Leu Leu Lys Gln Tyr Gly Phe Pro Arg Arg Pro Pro Pro
                165                 170                 175

Arg Gly Ser Gln Ala Ala Gln Gly Gly Pro Ala Lys Gln Leu Leu Pro
            180                 185                 190

Leu Glu Arg Val Tyr Gln Glu Ile Ala Ile Leu Lys Lys Leu Asp His
        195                 200                 205

Val Asn Val Val Lys Leu Ile Glu Val Leu Asp Asp Pro Ala Glu Asp

```
                210                 215                 220

Asn Leu Tyr Leu Val Phe Asp Leu Leu Arg Lys Gly Pro Val Met Glu
225                 230                 235                 240

Val Pro Cys Asp Lys Pro Phe Ser Glu Glu Gln Ala Arg Leu Tyr Leu
                245                 250                 255

Arg Asp Val Ile Leu Gly Leu Glu Tyr Leu His Cys Gln Lys Ile Val
            260                 265                 270

His Arg Asp Ile Lys Pro Ser Asn Leu Leu Gly Asp Asp Gly His
        275                 280                 285

Val Lys Ile Ala Asp Phe Gly Val Ser Asn Gln Phe Glu Gly Asn Asp
    290                 295                 300

Ala Gln Leu Ser Ser Thr Ala Gly Thr Pro Ala Phe Met Ala Pro Glu
305                 310                 315                 320

Ala Ile Ser Asp Ser Gly Gln Ser Phe Ser Gly Lys Ala Leu Asp Val
                325                 330                 335

Trp Ala Thr Gly Val Thr Leu Tyr Cys Phe Val Tyr Gly Lys Cys Pro
            340                 345                 350

Phe Ile Asp Asp Phe Ile Leu Ala Leu His Arg Lys Ile Lys Asn Glu
        355                 360                 365

Pro Val Val Phe Pro Glu Glu Pro Glu Ile Ser Glu Glu Leu Lys Asp
    370                 375                 380

Leu Ile Leu Lys Met Leu Asp Lys Asn Pro Glu Thr Arg Ile Gly Val
385                 390                 395                 400

Pro Asp Ile Lys Leu His Pro Trp Val Thr Lys Asn Gly Glu Glu Pro
                405                 410                 415

Leu Pro Ser Glu Glu Glu His Cys Ser Val Val Glu Val Thr Glu Glu
            420                 425                 430

Glu Val Lys Asn Ser Val Arg Leu Ile Pro Ser Trp Thr Thr Val Ile
        435                 440                 445

Leu Val Lys Ser Met Leu Arg Lys Arg Asp Phe Gly Asn Pro Phe Glu
    450                 455                 460

Pro Gln Ala Arg Arg Glu Glu Arg Ser Met Ser Ala Pro Gly Asn Leu
465                 470                 475                 480

Leu Val Lys Glu Gly Phe Gly Glu Gly Gly Lys Ser Pro Glu Leu Pro
                485                 490                 495

Gly Val Gln Glu Asp Glu Ala Ala Ser
            500                 505

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
ggauucuaug augaaacuct t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 12
gaguuucauc auagaaucct g                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
gcaccaucaa agaaggaaat t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
uuuccuucuu ugauggugct t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
ggugauggug uaaaauacat t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
uguauuuuac accaucacct t                                              21

<210> SEQ ID NO 17
<211> LENGTH: 88
<212> TYPE: DNA
<213> ORGANISM: Homo sapiens
```

```
<400> SEQUENCE: 17
caccttgtcc tcacggtcca gttttcccag gaatcccta gatgctaaga tggggattcc        60
tggaaatact gttcttgagg tcatggtt                                          88
```